(12) United States Patent
Kessler et al.

(10) Patent No.: US 9,526,519 B2
(45) Date of Patent: Dec. 27, 2016

(54) TISSUE-REMOVING CATHETER WITH IMPROVED ANGULAR TISSUE-REMOVING POSITIONING WITHIN BODY LUMEN

(71) Applicant: Covidien LP, Mansfield, MA (US)

(72) Inventors: Jason Kessler, Minneapolis, MN (US); Lucas Schneider, Champlin, MN (US)

(73) Assignee: Covidien LP, Mansfield, MA (US)

(*) Notice: Subject to any disclaimer, the term of this patent is extended or adjusted under 35 U.S.C. 154(b) by 342 days.

(21) Appl. No.: 14/170,832

(22) Filed: Feb. 3, 2014

(65) Prior Publication Data

US 2015/0216553 A1    Aug. 6, 2015

(51) Int. Cl.
*A61B 17/3207* (2006.01)

(52) U.S. Cl.
CPC ... *A61B 17/320758* (2013.01); *A61B 17/3207* (2013.01); *A61B 17/320783* (2013.01); *A61B 2017/320791* (2013.01); *A61B 2034/2048* (2016.02); *A61B 2090/067* (2016.02)

(58) Field of Classification Search
CPC .................. A61B 17/3207; A61B 17/320725; A61B 17/32075; A61B 17/320758; A61B 17/320783; A61B 2017/00017; A61B 2017/320791; A61B 2017/320733; A61B 2017/320741; A61B 10/02; A61B 10/0233; A61B 10/0241; A61B 10/025; A61B 10/0266; A61B 10/0275; A61B 10/0291; A61B 2010/0258

See application file for complete search history.

(56) References Cited

U.S. PATENT DOCUMENTS

| | | |
|---|---|---|
| 1,481,078 A | 1/1924 | Albertson |
| 2,701,559 A | 2/1955 | Cooper |
| 2,850,007 A | 9/1958 | Lingley |
| 3,064,651 A | 11/1962 | Henderson |

(Continued)

FOREIGN PATENT DOCUMENTS

| | | |
|---|---|---|
| CA | 2000621 A1 | 4/1990 |
| EP | 0 086 048 A2 | 8/1983 |

(Continued)

OTHER PUBLICATIONS

International Search Report and Written Opinion for Application No. PCT/US2015/014167 dated May 4, 2015, 16 pages.

*Primary Examiner* — David C Eastwood

(57) ABSTRACT

A tissue-removing catheter for removing tissue from a body lumen includes a tissue-removing. The tissue-removing element may be coupled to a first longitudinal body portion of the catheter body. The first longitudinal body portion may be rotatable along its length and relative to a second longitudinal body portion to adjust the angular position of the first longitudinal body portion relative to the second longitudinal body portion. An angular-positioning mechanism may be operatively connected to the tissue-removing element for rotating the tissue-removing element relative to the second longitudinal body portion about a rotational axis to adjust an angular tissue-removing position of the tissue-removing element, relative to the longitudinal axis of the body lumen, from an first angular tissue-removing position to a second angular tissue-removing position offset from the first angular tissue-removing position.

17 Claims, 17 Drawing Sheets

(56) References Cited

U.S. PATENT DOCUMENTS

| | | |
|---|---|---|
| 3,082,805 A | 3/1963 | Royce |
| 3,614,953 A | 10/1971 | Moss |
| 3,683,891 A | 8/1972 | Eskridge et al. |
| 3,732,858 A | 5/1973 | Banko |
| 3,749,085 A | 7/1973 | Willson et al. |
| 3,800,783 A | 4/1974 | Jamshidi |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 4,007,732 A | 2/1977 | Kvavle et al. |
| 4,020,847 A | 5/1977 | Clark, III |
| 4,030,503 A | 6/1977 | Clark, III |
| 4,038,985 A | 8/1977 | Chiulli |
| 4,112,708 A | 9/1978 | Fukuda |
| 4,177,797 A | 12/1979 | Baylis et al. |
| 4,273,128 A | 6/1981 | Lary |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,732,154 A | 3/1988 | Shiber |
| 4,745,919 A | 5/1988 | Bundy et al. |
| 4,747,406 A | 5/1988 | Nash |
| 4,747,821 A | 5/1988 | Kensey et al. |
| 4,754,755 A | 7/1988 | Husted |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,819,634 A | 4/1989 | Shiber |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,490 A | 12/1989 | Shiber |
| 4,887,613 A | 12/1989 | Farr et al. |
| 4,894,051 A | 1/1990 | Shiber |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,950,238 A | 8/1990 | Sullivan |
| 4,957,482 A | 9/1990 | Shiber |
| 4,966,604 A | 10/1990 | Reiss |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,026,384 A | 6/1991 | Farr et al. |
| 5,030,201 A | 7/1991 | Palestrant |
| 5,047,040 A | 9/1991 | Simpson et al. |
| 5,049,124 A | 9/1991 | Bales, Jr. |
| 5,064,435 A | 11/1991 | Porter |
| 5,071,425 A | 12/1991 | Gifford, III et al. |
| 5,074,841 A | 12/1991 | Ademovic et al. |
| 5,077,506 A | 12/1991 | Krause |
| 5,078,722 A | 1/1992 | Stevens |
| 5,087,265 A | 2/1992 | Summers |
| 5,092,839 A | 3/1992 | Kipperman |
| 5,092,873 A | 3/1992 | Simpson et al. |
| 5,100,426 A | 3/1992 | Nixon |
| 5,112,345 A | 5/1992 | Farr |
| 5,114,399 A | 5/1992 | Kovalcheck |
| 5,135,531 A | 8/1992 | Shiber |
| 5,154,705 A | 10/1992 | Fleischhacker et al. |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,192,291 A | 3/1993 | Pannek, Jr. |
| 5,195,956 A | 3/1993 | Stockmeier |
| 5,222,966 A | 6/1993 | Perkins et al. |
| 5,224,945 A | 7/1993 | Pannek, Jr. |
| 5,242,460 A | 9/1993 | Klein et al. |
| 5,242,461 A | 9/1993 | Kortenbach et al. |
| 5,263,959 A | 11/1993 | Fischell |
| 5,267,955 A | 12/1993 | Hanson |
| 5,269,793 A | 12/1993 | Simpson |
| 5,273,526 A | 12/1993 | Dance et al. |
| 5,284,486 A | 2/1994 | Kotula et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,314,438 A | 5/1994 | Shturman |
| 5,322,508 A | 6/1994 | Viera |
| 5,324,300 A | 6/1994 | Elias et al. |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,366,463 A | 11/1994 | Ryan |
| 5,370,609 A | 12/1994 | Drasler et al. |
| 5,370,651 A | 12/1994 | Summers |
| 5,372,601 A | 12/1994 | Lary |
| 5,373,619 A | 12/1994 | Fleischhacker et al. |
| 5,378,234 A | 1/1995 | Hammerslag et al. |
| 5,395,311 A | 3/1995 | Andrews |
| 5,395,335 A | 3/1995 | Jang |
| 5,397,345 A | 3/1995 | Lazarus |
| 5,403,334 A | 4/1995 | Evans et al. |
| 5,409,454 A | 4/1995 | Fischell et al. |
| 5,423,740 A | 6/1995 | Sullivan |
| 5,423,799 A | 6/1995 | Shiu |
| 5,423,846 A | 6/1995 | Fischell |
| 5,431,673 A | 7/1995 | Summers et al. |
| 5,441,510 A | 8/1995 | Simpson et al. |
| 5,443,497 A | 8/1995 | Venbrux |
| 5,451,233 A | 9/1995 | Yock |
| 5,454,809 A | 10/1995 | Janssen |
| 5,489,295 A | 2/1996 | Piplani et al. |
| 5,496,267 A | 3/1996 | Drasler et al. |
| 5,501,694 A | 3/1996 | Ressemann et al. |
| 5,507,292 A | 4/1996 | Jang et al. |
| 5,507,760 A | 4/1996 | Wynne et al. |
| 5,507,761 A | 4/1996 | Duer |
| 5,512,044 A | 4/1996 | Duer |
| 5,514,115 A | 5/1996 | Frantzen et al. |
| 5,522,825 A | 6/1996 | Kropf et al. |

(56) References Cited

U.S. PATENT DOCUMENTS

| | | |
|---|---|---|
| 5,522,880 A | 6/1996 | Barone et al. |
| 5,531,690 A | 7/1996 | Solar |
| 5,554,163 A | 9/1996 | Shturman |
| 5,556,408 A | 9/1996 | Farhat |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,571,130 A | 11/1996 | Simpson et al. |
| 5,575,787 A * | 11/1996 | Abela ............ A61B 18/24 606/11 |
| 5,575,817 A | 11/1996 | Martin |
| 5,584,843 A | 12/1996 | Wulfman et al. |
| 5,609,605 A | 3/1997 | Marshall et al. |
| 5,618,293 A | 4/1997 | Sample et al. |
| 5,624,457 A | 4/1997 | Farley et al. |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,643,296 A | 7/1997 | Hundertmark et al. |
| 5,649,941 A | 7/1997 | Lary |
| 5,662,671 A | 9/1997 | Barbut et al. |
| 5,665,098 A | 9/1997 | Kelly et al. |
| 5,669,920 A | 9/1997 | Conley et al. |
| 5,676,696 A | 10/1997 | Marcade |
| 5,676,697 A | 10/1997 | McDonald |
| 5,681,336 A | 10/1997 | Clement et al. |
| 5,683,449 A | 11/1997 | Marcade |
| 5,683,453 A | 11/1997 | Palmaz |
| 5,695,506 A | 12/1997 | Pike et al. |
| 5,695,507 A | 12/1997 | Auth et al. |
| 5,697,944 A | 12/1997 | Lary |
| 5,700,240 A | 12/1997 | Barwick, Jr. et al. |
| 5,707,350 A | 1/1998 | Krause et al. |
| 5,707,383 A | 1/1998 | Bays et al. |
| 5,713,913 A | 2/1998 | Lary et al. |
| 5,728,123 A | 3/1998 | Lemelson et al. |
| 5,733,296 A | 3/1998 | Rogers et al. |
| 5,735,816 A | 4/1998 | Lieber et al. |
| 5,766,192 A | 6/1998 | Zacca |
| 5,772,674 A | 6/1998 | Nakhjavan |
| 5,776,153 A | 7/1998 | Rees |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,807,329 A | 9/1998 | Gelman |
| 5,820,592 A | 10/1998 | Hammerslag |
| 5,824,039 A | 10/1998 | Piplani et al. |
| 5,824,055 A | 10/1998 | Spiridigliozzi et al. |
| 5,827,229 A | 10/1998 | Auth et al. |
| 5,827,304 A | 10/1998 | Hart |
| 5,827,322 A | 10/1998 | Williams |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,871,536 A | 2/1999 | Lazarus |
| 5,873,882 A | 2/1999 | Straub et al. |
| 5,876,414 A | 3/1999 | Straub |
| 5,938,645 A | 8/1999 | Gordon |
| 5,938,672 A | 8/1999 | Nash |
| 5,941,869 A | 8/1999 | Patterson et al. |
| 6,001,112 A | 12/1999 | Taylor |
| 6,027,514 A | 2/2000 | Stine et al. |
| 6,032,673 A | 3/2000 | Savage et al. |
| 6,095,990 A | 8/2000 | Parodi |
| 6,152,909 A | 11/2000 | Bagaoisan et al. |
| 6,156,046 A | 12/2000 | Passafaro et al. |
| 6,159,195 A | 12/2000 | Ha et al. |
| 6,206,898 B1 | 3/2001 | Honeycutt et al. |
| 6,238,405 B1 | 5/2001 | Findlay, III et al. |
| 6,299,622 B1 | 10/2001 | Snow et al. |
| 6,312,444 B1 | 11/2001 | Barbut |
| 6,447,525 B2 | 9/2002 | Follmer et al. |
| 6,451,036 B1 | 9/2002 | Heitzmann et al. |
| 6,454,779 B1 | 9/2002 | Taylor |
| 6,482,217 B1 | 11/2002 | Pintor et al. |
| 6,565,588 B1 | 5/2003 | Clement et al. |
| 6,623,437 B2 | 9/2003 | Hinchliffe et al. |
| 6,623,495 B2 | 9/2003 | Findlay, III et al. |
| 6,638,233 B2 | 10/2003 | Corvi et al. |
| 6,652,505 B1 | 11/2003 | Tsugita |
| 6,656,195 B2 | 12/2003 | Peters et al. |
| 6,666,874 B2 | 12/2003 | Heitzmann et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,843,797 B2 | 1/2005 | Nash et al. |
| 6,849,068 B1 | 2/2005 | Bagaoisan et al. |
| 7,172,610 B2 | 2/2007 | Heitzmann et al. |
| 7,235,088 B2 | 6/2007 | Pintor et al. |
| 7,479,147 B2 | 1/2009 | Honeycutt |
| 7,771,445 B2 | 8/2010 | Heitzmann et al. |
| 7,842,055 B2 | 11/2010 | Pintor et al. |
| 7,981,128 B2 * | 7/2011 | To .............. A61B 17/320758 606/159 |
| 9,241,734 B2 * | 1/2016 | Ladd ........... A61B 17/320758 |
| 2001/0004700 A1 | 6/2001 | Honeycutt et al. |
| 2001/0044622 A1 | 11/2001 | Vardi |
| 2002/0058904 A1 | 5/2002 | Boock |
| 2002/0077642 A1 * | 6/2002 | Patel ............ A61B 17/320758 606/167 |
| 2002/0095141 A1 | 7/2002 | Belef |
| 2002/0177800 A1 | 11/2002 | Bagaoisan |
| 2003/0023263 A1 | 1/2003 | Krolik |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0087988 A1 | 5/2004 | Heitzmann et al. |
| 2005/0004594 A1 | 1/2005 | Nool |
| 2006/0235334 A1 | 10/2006 | Corvi et al. |
| 2006/0259052 A1 | 11/2006 | Pintor et al. |
| 2007/0010840 A1 * | 1/2007 | Rosenthal ........ A61B 17/3207 606/170 |
| 2007/0225739 A1 | 9/2007 | Pintor et al. |
| 2007/0270686 A1 * | 11/2007 | Ritter ............ A61B 5/06 600/424 |
| 2008/0065125 A1 * | 3/2008 | Olson ........... A61B 17/320758 606/159 |
| 2009/0018567 A1 * | 1/2009 | Escudero ....... A61B 17/320758 606/159 |
| 2009/0024085 A1 * | 1/2009 | To .............. A61B 17/320758 604/95.01 |
| 2010/0174302 A1 | 7/2010 | Heitzmann et al. |
| 2012/0123352 A1 | 5/2012 | Fruland et al. |

FOREIGN PATENT DOCUMENTS

| | | |
|---|---|---|
| EP | 0 291 170 A1 | 11/1988 |
| EP | 0 330 843 A1 | 9/1989 |
| EP | 0 373 927 A2 | 6/1990 |
| EP | 0 421 457 A1 | 4/1991 |
| EP | 0 448 859 A2 | 10/1991 |
| EP | 0 463 798 A1 | 1/1992 |
| EP | 0 514 810 A1 | 11/1992 |
| EP | 0 533 320 A2 | 3/1993 |
| EP | 0 657 140 A1 | 6/1995 |
| GB | 2 093 353 A | 9/1982 |
| GB | 2 210 965 A | 6/1989 |
| JP | 2-271847 A | 11/1990 |
| JP | 3-186256 A | 8/1991 |
| JP | 4-200459 A | 7/1992 |
| JP | 5-42162 A | 2/1993 |
| JP | 5-56984 A | 3/1993 |
| JP | 5-184679 A | 7/1993 |
| JP | 6-205785 A | 7/1994 |
| JP | 6-269460 A | 9/1994 |
| JP | 11-347040 A | 12/1999 |

(56) References Cited

FOREIGN PATENT DOCUMENTS

| | | |
|---|---|---|
| WO | WO 89/06517 A1 | 8/1989 |
| WO | WO 93/13716 A1 | 7/1993 |
| WO | WO 93/13717 A1 | 7/1993 |
| WO | WO 94/11053 A1 | 5/1994 |
| WO | WO 95/21576 A1 | 8/1995 |
| WO | WO 96/11648 A1 | 4/1996 |
| WO | WO 97/46164 A1 | 12/1997 |
| WO | WO 98/04199 A1 | 2/1998 |
| WO | WO 98/24372 A1 | 6/1998 |
| WO | WO 98/24373 A1 | 6/1998 |
| WO | WO 99/52454 A1 | 10/1999 |
| WO | WO 01/30433 A1 | 5/2001 |
| WO | WO 01/43809 A1 | 6/2001 |
| WO | 2010107424 A1 | 9/2010 |
| WO | WO 2010107424 A1 * | 9/2010 ......... A61B 10/0275 |

* cited by examiner

TISSUE-REMOVING CATHETER WITH IMPROVED ANGULAR TISSUE-REMOVING POSITIONING WITHIN BODY LUMEN

FIELD OF THE DISCLOSURE

The present disclosure generally relates to a tissue-removing catheter having improved angular tissue-removing positioning within a body lumen.

BACKGROUND OF THE DISCLOSURE

Debulking or tissue-removing catheters are used to remove unwanted tissue from the body. As an example, atherectomy catheters are used to remove material from a blood vessel to open the blood vessel and improve blood flow through the vessel.

SUMMARY OF THE DISCLOSURE

In one aspect, a tissue-removing catheter for removing tissue from a body lumen includes a tissue-removing element. The tissue-removing element may be coupled to a first longitudinal body portion of the catheter body. The first longitudinal body portion may be rotatable along its length and relative to a second longitudinal body portion to adjust the angular position of the first longitudinal body portion relative to the second longitudinal body portion. An angular-positioning mechanism may be operatively connected to the tissue-removing element for rotating the tissue-removing element relative to the second longitudinal body portion about a rotational axis to adjust an angular tissue-removing position of the tissue-removing element, relative to the longitudinal axis of the body lumen, from a first angular tissue-removing position to a second angular tissue-removing position offset from the first angular tissue-removing position.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DISCLOSURE

Embodiments of a tissue-removing catheter having improved angular tissue-removing positioning within a body lumen for removing tissue from the body lumen are disclosed. In particular, the illustrated catheter embodiments are particularly suitable for removing (i.e., excising) plaque tissue from a blood vessel (e.g., peripheral arterial or peripheral venous wall). Features of the disclosed embodiments, however, may also be suitable for treating chronic total occlusion (CTO) of blood vessels, particularly peripheral arteries, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward catheters for removing tissue from, and penetrating occlusions in, blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Figure 1:
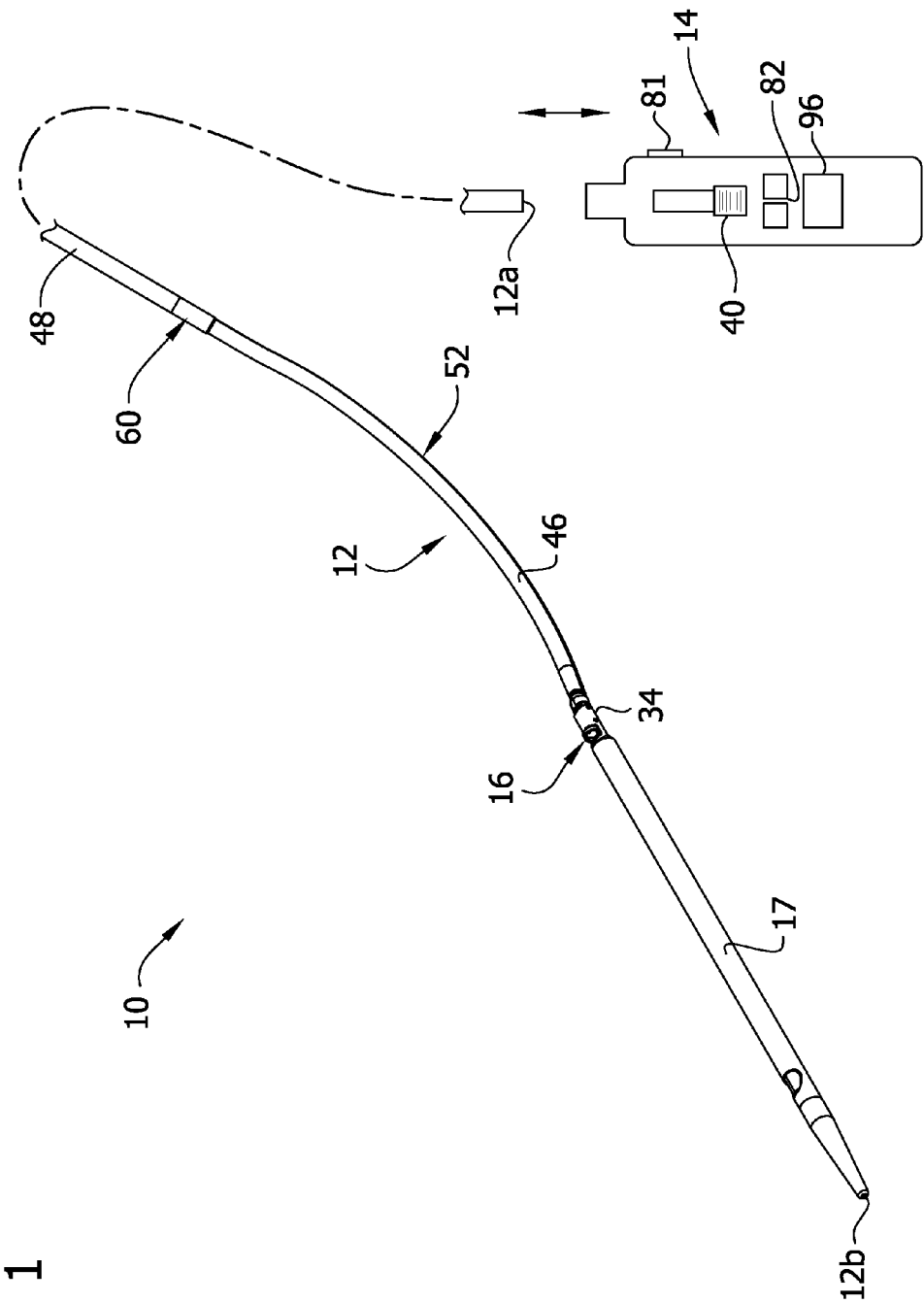
FIG. 1 is a perspective of a catheter body and a schematic representation of a handle, each of which are part of a catheter.

Referring to FIG. 1, a tissue-removing catheter, in accordance with one or more embodiments of the present disclosure, is generally indicated at reference numeral 10. The catheter 10 comprises an elongate catheter body, generally indicated at 12, having opposite proximal and distal ends 12a, 12b, respectively, and a longitudinal axis A1 (FIG. 3) extending between the proximal and distal ends. A handle or control unit, generally indicated at 14, is attachable to the proximal end 21a of the catheter body 12, although the handle may be fixedly attached to the catheter body in other embodiments. A tissue-removing element, generally indicated at 16, generally adjacent the distal end 12b of the catheter body 12, is configured to remove (e.g., cut) tissue from the body lumen and direct the removed tissue into a tissue container 17.

Figure 2:
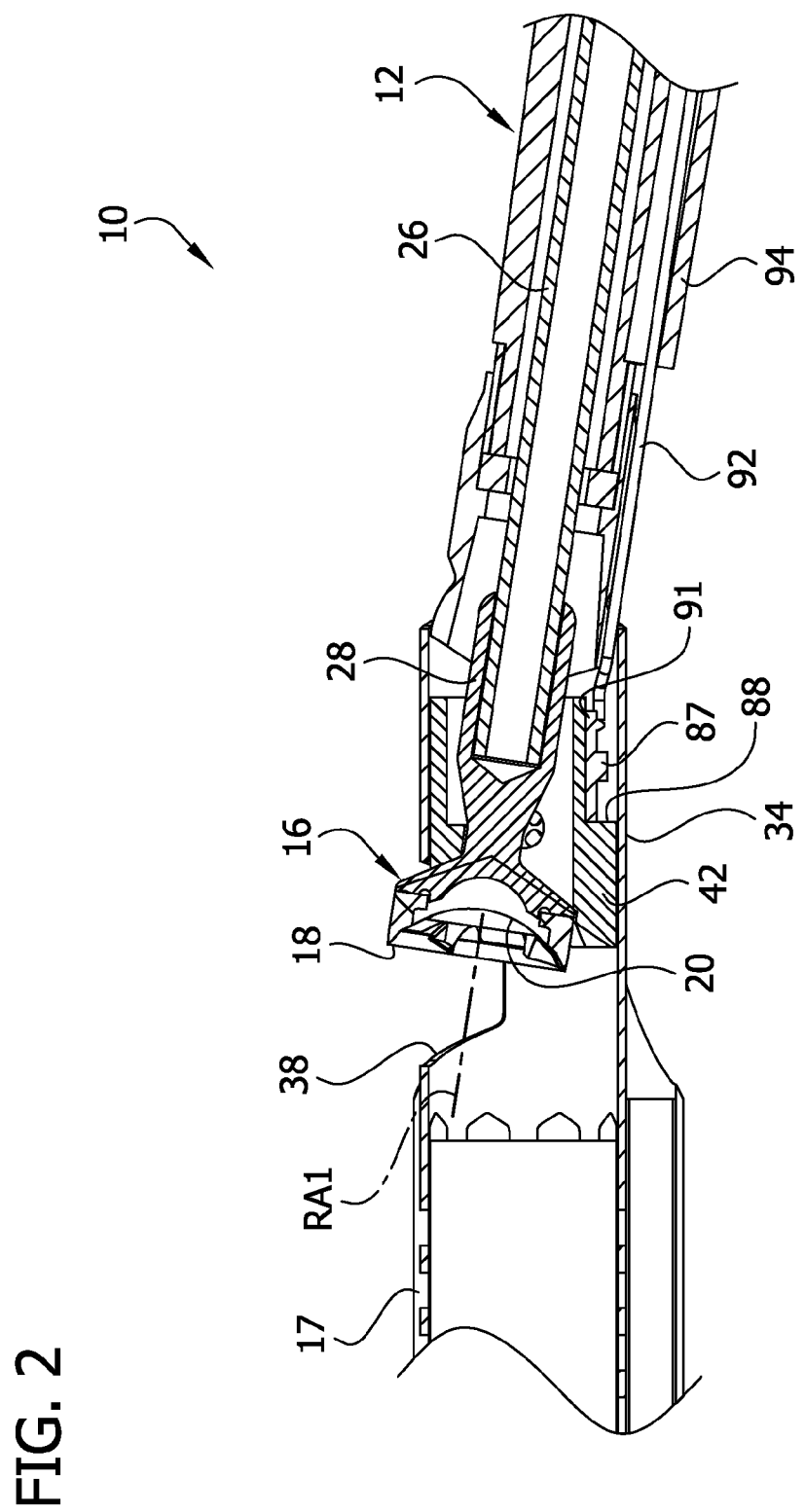
FIG. 2 is an enlarged fragmentary cross section of the catheter body, illustrating a tissue-removing element in a deployed position.

Referring to FIG. 2, in the illustrated embodiment, the tissue-removing element 16 comprises a rotatable cutting element that is rotatable about a rotation axis RA1 for cutting tissue. The illustrated cutting element 16 has a cutting edge 18 facing distally, although in other embodiments the cutting edge may face proximally, and a cup-shaped surface 20 for directing removed tissue distally into the tissue container 17 of the catheter body 12. In other embodiments, the tissue-removing element may have other configurations for cutting tissue, or may be configured to remove tissue in other ways. For example, the tissue-removing element may be configured to ablate tissue, or abrade tissue, or otherwise remove tissue from the body lumen. Moreover, the tissue-removing element may not be rotatable relative to the catheter body.

Referring still to FIG. 2, a tissue-removing driveshaft 26 is operatively connected to a stem 28 of the tissue-removing element 16 (e.g., fixedly secured thereto) for imparting rotation to the tissue-removing element. The tissue-removing driveshaft 26 (e.g., a coiled driveshaft) extends through the catheter body 12 and is operatively connectable to an electric driveshaft motor 30 (FIG. 10), or other prime mover, in the handle 14 for driving rotation of the driveshaft, and in turn, driving rotation of the tissue-removing element 16, relative to the catheter body. The driveshaft motor 30 is electrically connected to a power source 21 (FIG. 10) in the handle 14. In the illustrated embodiment, the driveshaft 26 is movable longitudinally within the catheter body 12 to impart longitudinal movement of the tissue-removing element 16 relative to the catheter body. Longitudinal movement of the tissue-removing element 16 actuates deployment and storage of the tissue-removing element relative to a tissue-removing housing 34, which is part of the catheter body 12. The tissue-removing housing 34 (e.g., a proximal end portion thereof) pivots about a pivot axis PA (FIG. 3) that is generally transverse to the longitudinal axis A1 of the catheter body. A distal portion of the housing 34 forms the tissue container 17, although the housing and the tissue collection chamber may be formed separately.

The tissue-removing element 16 is movable between a stored position (not shown) and a deployed position (FIGS. 1 and 2). In the stored position, the tissue-removing element 16 is received in the housing 34 and is not exposed through a window or side opening 38 of the housing. To deploy the tissue-removing element 16, the driveshaft 26 is moved proximally relative to the catheter body 12, such as by moving a lever or other actuator 40 (FIG. 1) on the handle 14 that is operatively connected to the driveshaft, to impart proximal movement of the tissue-removing element 16 relative to the housing 34. Referring to FIG. 2, as the tissue-removing element 16 moves proximally, the tissue-removing element, which acts as a cam, engages and moves longitudinally along an internal cam follower 42 of the housing 34, causing the housing to pivot about the pivot axis PA (FIG. 4) and the tissue-removing element to extend partially out of the window 38. A switch 43 (FIG. 11) may be coupled to the actuator 40 such that the driveshaft motor 30 activates (i.e., turns on) to impart rotation to the driveshaft 26 when the tissue-removing element 16 is deployed. To return the tissue-removing element 16 to its stored, non-deployed position, the driveshaft 26 is moved distally, such as by moving the actuator 40 distally, to impart distal movement of the tissue-removing element 16 along the cam follower 42. Distal movement of the tissue-removing element 16 causes the housing 34 to pivot or deflect back about the pivot axis PA so that the tissue-removing element is received in the housing 34 and does not extend outside the window 38. When the tissue-removing element 16 is in its stored position, the driveshaft motor 30 is deactivated (i.e., turned off). It is understood that a catheter 10 constructed according to the principles of the present disclosure may not include a deployment mechanism (e.g., the tissue-removing element or other functional element may always be deployed or may remain within the catheter body).

Figure 3:
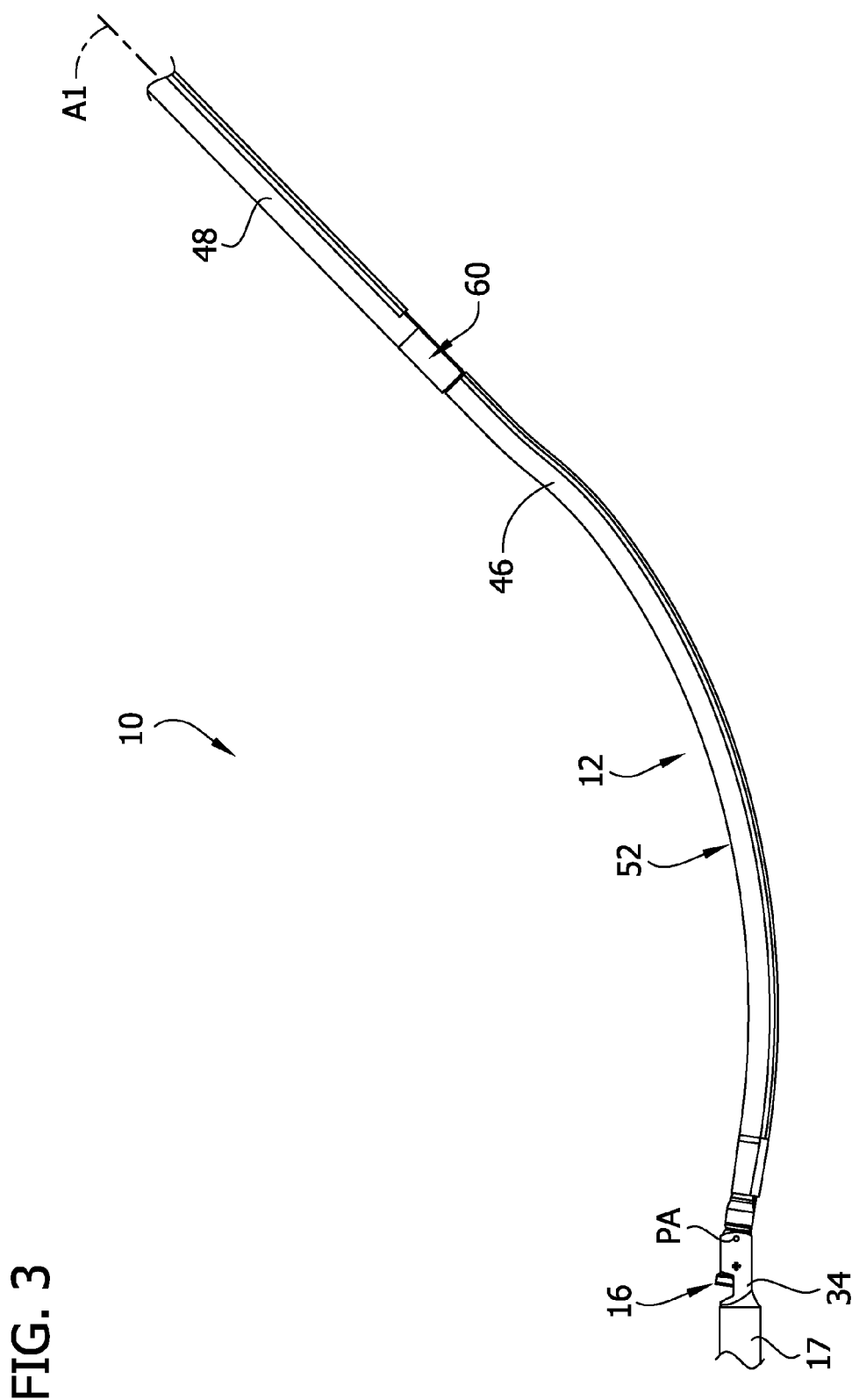
FIG. 3 is an enlarged fragmentary side elevation of the catheter body.
Figure 5:
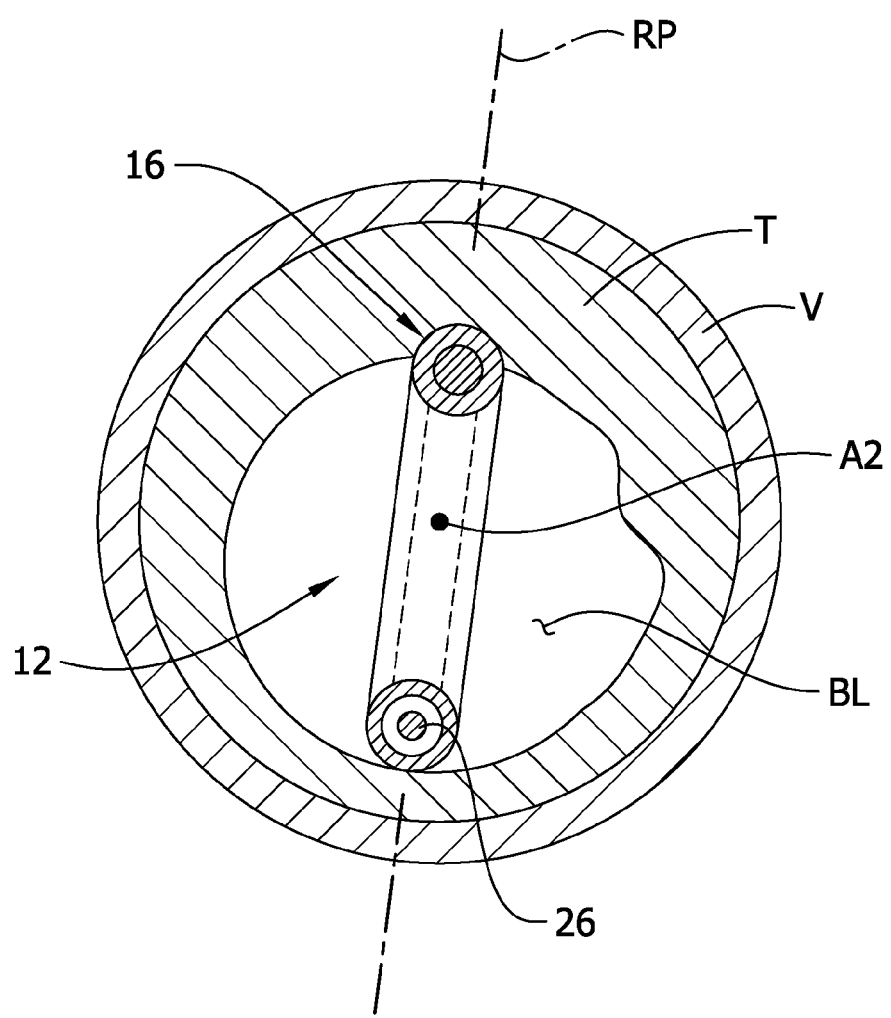
FIG. 5 is a schematic cross section of the catheter body received in a blood vessel taken in the plane defined by the line 5-5 in FIG. 4.

Referring to FIG. 3, the catheter body 12 includes a first (distal) longitudinal body portion 46 defining a distal portion of the catheter body, and a second (proximal) longitudinal body portion 48 that is proximal of the first (distal) longitudinal body portion. In the illustrated embodiment, the second (proximal) longitudinal body portion 48 extends from adjacent a proximal end of the first (distal) longitudinal body portion 46 toward the proximal end 12a of the catheter body 12. As explained in more detail below, the first (distal) longitudinal body portion 46 is selectively rotatable along its length and relative to the second (proximal) longitudinal body portion 48 about a second rotational axis A2 (FIG. 5). In particular, the first (distal) longitudinal body portion 46 is operatively connected to an angular-positioning mechanism 60 for imparting rotation of the first (distal) longitudinal body portion along its length and relative to the second (proximal) longitudinal body portion 48. The first and second (proximal) longitudinal body portions 46, 48, respectively, are suitably flexible for navigating the catheter body 12 through tortuous paths within the body lumen BL. The first (distal) longitudinal body portion 46 may comprise a torque tube (e.g., a coiled member) for transmitting torque from its proximal end toward its distal end, as explained in more detail below. In particular, the torque tube of the first longitudinal portion 46 may be formed from coiled stainless steel or other materials and constructions. The second (proximal) longitudinal body portion 48 may also comprise a torque tube, although for reasons explained in more detail below, the second (proximal) longitudinal body portion may not include a torque tube as it may not be necessary for the second (proximal) longitudinal body portion to be capable of effectively transmitting torque from its proximal end toward its distal end.

Referring still to FIG. 3, the catheter 10 comprises an apposition member, generally indicated at 52, that is configured to apply an apposition force in a generally radial direction relative to a longitudinal axis A1 of the catheter body 12 to direct the tissue-removing element 16 toward a peripheral (or circumferential) portion of the body lumen when the catheter is inserted in the body lumen BL defined by the blood vessel V. In the illustrated embodiment, the apposition member 52 comprises a jogged portion of the first (distal) longitudinal body portion 46 that is biased or pre-formed in a jogged or curved configuration. In other embodiments, the apposition member 52 may be of other constructions for directing the tissue-removing element 16 toward a peripheral portion of the body lumen BL. For example, in other embodiments the apposition member may comprise an inflatable member secured adjacent the tissue-removing element 16 on a side of the housing 34 that is opposite the window 38. In other embodiments, the housing 34 may function as the apposition member, whereby pivoting of the housing directs the tissue-removing element 16 toward a peripheral or circumferential portion of the body lumen. The apposition member may be of other constructions.

Figure 4:
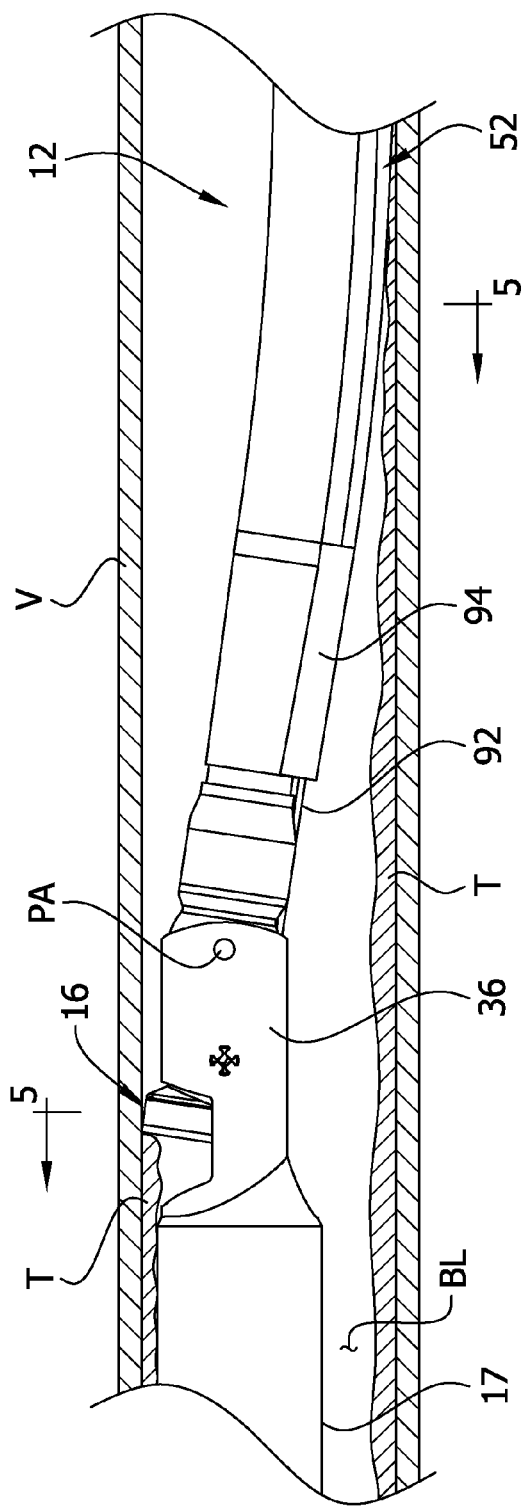
FIG. 4 is an enlarged fragmentary side elevation of the catheter body received in a blood vessel shown in section.

As can be seen in FIG. 4, when the catheter 10 is inserted in the body lumen BL, the apposition member 52 engages a peripheral portion of the body lumen BL defined by the blood vessel V to maintain the tissue-removing element 16 and/or the window 38 (FIG. 2) in apposition with an opposite peripheral portion of the body lumen that is generally diametrically opposite (e.g., 180 degrees from) the peripheral portion engaged by the apposition member. This angular position of the tissue-removing element 16 relative to the longitudinal axis A2 of the body lumen BL is referred to herein as the "angular tissue-removing position." In the schematic of FIG. 5, the angular position of the tissue-removing element 16 is offset 0 degrees from a reference plane RP passing through the body lumen BL. In general, the angular tissue-removing position of a tissue-removing element 16 is about 180 degrees offset from the location of the force applied to the body lumen BL by the apposition member.

Figure 6:
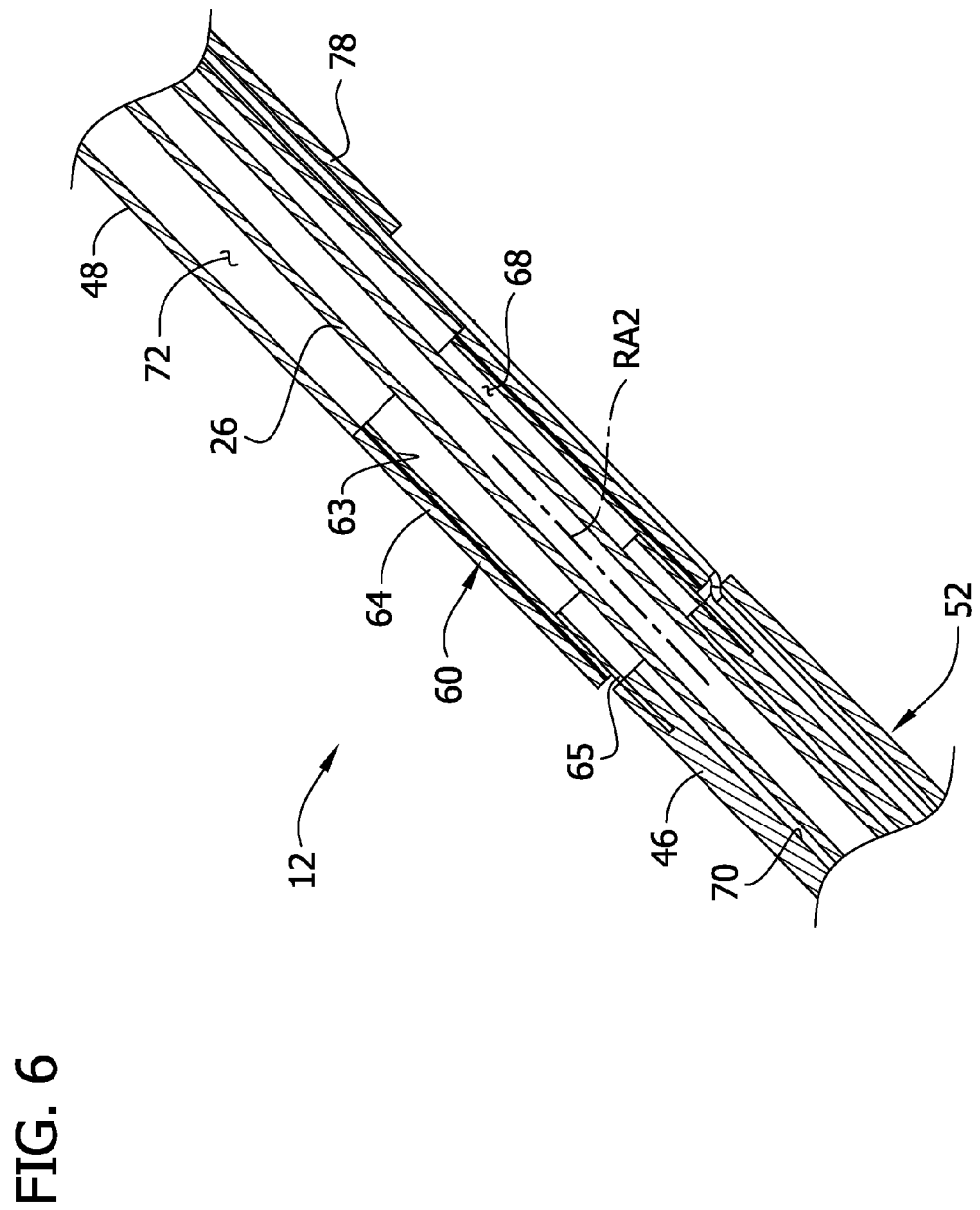
FIG. 6 is an enlarged fragmentary section taken in the plane defined by the line 6-6 in FIG. 8.

Referring to FIG. 6, the angular-positioning mechanism 60 allows the user to rotate the apposition member 52 (and this the tissue-removing element 16) within the body lumen BL to adjust the angular tissue-removing position of the tissue-removing element relative to the longitudinal axis A2 of the body lumen, without manually rotating or torqueing the second (proximal) longitudinal body portion 48 of the catheter body. In particular, the angular-positioning mechanism 60 is operatively connected to the apposition member 52 and configured to rotate the apposition member relative to the second (proximal) longitudinal body portion 48 of the catheter body 12 about the rotational axis A2 to adjust the angular tissue-removing position of the tissue-removing element relative to the longitudinal axis A2 of the body lumen BL when the catheter 10 is inserted in the body lumen. In the illustrated embodiment, the angular-positioning mechanism 60 includes a prime mover, such as an electric motor, located between the first (distal) and second (proximal) longitudinal body portions 46, 48 and electrically connectable to a power source, such as the same power source 21 electrically connectable to the driveshaft motor 30, or a different power source. In particular, the illustrated angular-positioning motor 60 is a pass through electric motor including a rotor 63, a stator 64, and a hollow output shaft 65 connected to the first (distal) longitudinal body portion 46. The angular-positioning motor 60 has an opening 68 that is coaxial with lumens 70, 72 defined by the respective first (distal) and second (proximal) longitudinal body portions 46, 48. The driveshaft 26 passes through the opening 68 in the angular-positioning motor 60 and through the lumens 70, 72. The angular-positioning motor 60 may be other types of electric motors, or other types of prime movers. In other embodiments, the angular-positioning mechanism 60 may be located elsewhere on the catheter 10, such as another location on the catheter body 12 or in the handle 14, for rotating at least the first (distal) longitudinal body portion 46 about its length.

Figure 7:
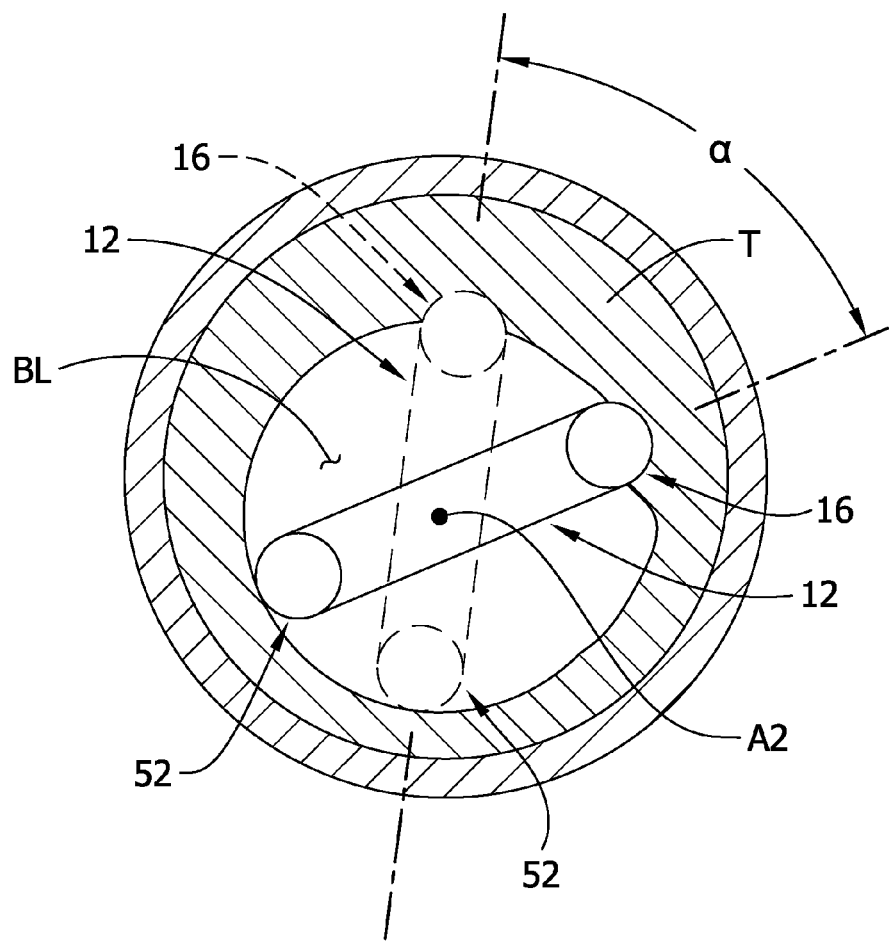
FIG. 7 is similar to FIG. 5, except illustrating a change in an angular tissue-removing position of the tissue-removing element of the catheter body.

Referring to FIG. 7, the illustrated apposition member 52 functions as an eccentric because it is not coaxial with (i.e., is off-center from) the rotational axis A2 of the angular-positioning mechanism 60. In effect, rotating the apposition member 52 about the rotational axis A2 adjusts the angular tissue-removing position relative to the body lumen BL and allows the user to direct the tissue-removing element 16 toward a different peripheral portion of the body lumen. For example, in the schematic illustration of FIG. 7, the apposition member 52 is rotated relative to the axis A2 of the body lumen BL so that the angular tissue-removing position of the tissue-removing element 16 (shown in solid lines) is offset an angle α, measuring about 60 degrees in the clockwise direction, from a reference tissue-removing position (shown in broken lines) of the tissue-removing element.

Figure 8:
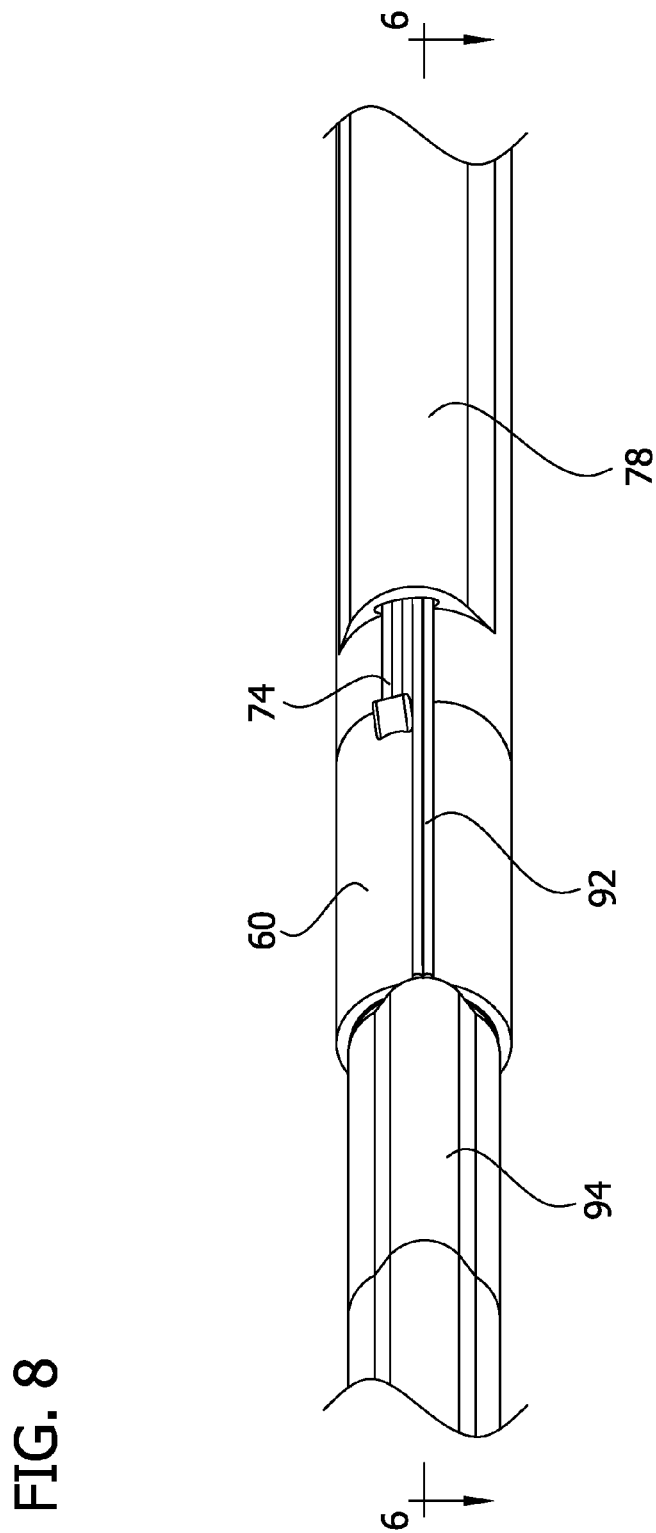
FIG. 8 is an enlarged fragmentary bottom elevation of the catheter body.

Referring to FIG. 8, the angular-positioning motor 60 is electrically connectable to the power source 21 via one or more electrical conductors 74, such as wires or flex circuits, running along the catheter body 12. In the illustrated embodiment, the electrical conductors 74 are received in a wire lumen 78 that is separate and free from communication with the driveshaft lumens 70, 72 of the catheter body 12. In other embodiments, the electrical conductors may be received in the driveshaft lumens 70, 72. The angular-positioning motor 60 may be powered in other ways, including a local battery or in other ways, whereby the electrical conductors may be omitted.

Figure 9:
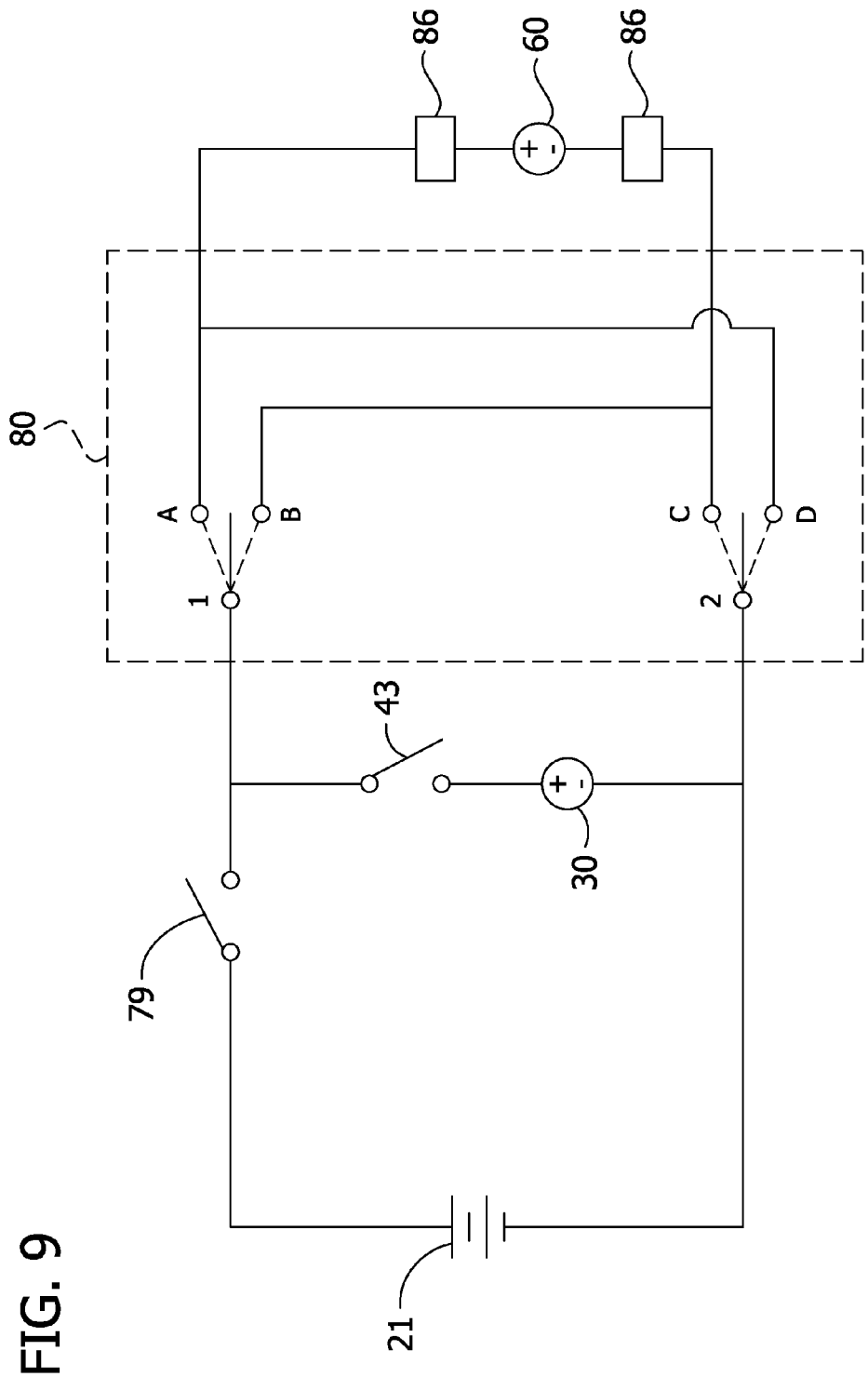
FIG. 9 is an electrical diagram of electrical components of the catheter according to one or more embodiments.
Figure 10:
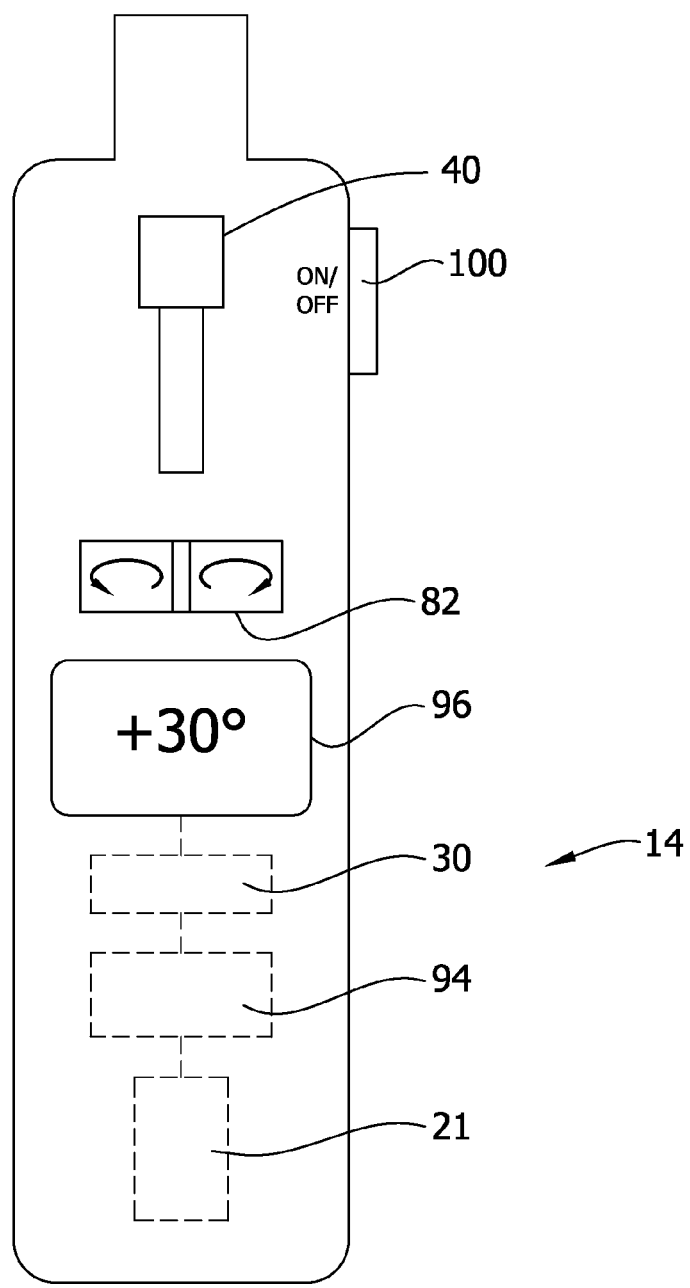
FIG. 10 is an enlarged schematic of the handle in FIG. 1.

An electrical schematic including the power source 21, the driveshaft motor 30, and the angular-positioning motor 60 is shown in FIG. 9. The catheter 10 includes a power switch 79 for selectively connecting the power source 21 to respective switches 43, 80 for the driveshaft motor 30 and the angular-positioning motor 60. In this illustrated embodiment, an actuator 81 (e.g., toggle, as illustrated, or a lever or slide or button), as shown in FIG. 10, is provided on the handle 14 to selectively actuate the switch 79. The switch 80 for selectively connecting the angular-positioning motor 60 to the electrical power source 21 to operate the angular-positioning motor may be a mechanical switch (as illustrated) or a solid-state switch or other types of switches. In this illustrated embodiment, an actuator 82 (e.g., toggle, as illustrated, or a lever or slide or button), as shown in FIG. 10, is provided on the handle 14 to selectively actuate the switch 80. In the embodiment illustrated in FIG. 9, the switch 80 allows the user to selectively control the direction of rotation of the angular-positioning motor 60 and the apposition member 52. As an example, the switch 80 may be a double pole center off switch. When the actuator 82 is in the "off" position (i.e., neither rotational direction is selected), the terminal sets 1A, 1B, 2C, and 2D are open and the angular-positioning motor 60 is not activated. To move the apposition member 52 in the clockwise direction (and thus adjust the angular tissue-removing position of the tissue-removing element 16 in the body lumen BL), the user selects the "clockwise" direction on the actuator 82. For example, the user may depress the right side of the illustrated toggle actuator 82, whereby the terminals sets 1A and 2C are closed and the terminal sets 1B and 2D are open. Electrical current flows through the closed terminal sets 1A and 2D powers rotation of the angular-positioning motor 60 in the clockwise direction to rotate the apposition member 52 in the clockwise direction. To move the apposition member 52 in the counterclockwise direction (and thus adjust the angular tissue-removing position of the tissue-removing element 16 in the body lumen BL), the user selects the "counterclockwise" direction on the actuator 82. For example, the user may depress the left side of the illustrated toggle actuator 82 to actuate closing of the terminals sets 1B and 2D, while the terminal sets 1A and 2C are open. Electrical current flows through the closed terminal sets 1B and 2D powers the angular-positioning motor 60 in the counterclockwise direction to rotate the apposition member in the counterclockwise direction.

Referring still to FIG. 9, one or more pulse width modulators (PWM) 86 are electrically connected to the angular-positioning motor 60 for regulating a duty cycle supplied to the angular-positioning motor from the power source 21. In this example, the electrical current is received from the same power source 21 as the driveshaft motor 30. The modulators 86 effectively regulate the duty cycle supplied to the angular-positioning motor 60 to regulate the rotational speed of the motor in either direction. It is envisioned that the one or more modulators 86 will regulate the speed of the angular-positioning motor 60 to substantially less than that of the driveshaft 26 (e.g., from about 1 rpm to about 60 rpm). The one or more modulators 86 may be received in the handle 14 or in the catheter body 12. It is understood that catheter may not include such a pulse with modulator 86 in other embodiments.

The switch 80 may be of other types of switches. For example, in the embodiment illustrated in FIG. 11, the switch 80' is a single pole, single throw switch, whereby when the switch is on (i.e., the circuit path is closed) power is supplied to the angular-positioning motor 60 (the angular-positioning motor is on and operating), and when the switch is off (i.e., the circuit path is open) power is interrupted to the angular-positioning motor (the angular-positioning motor is off and non-operating). In this embodiment, the angular-positioning motor 60 is configured to rotate in only one-direction (e.g., clockwise).

Figure 12:
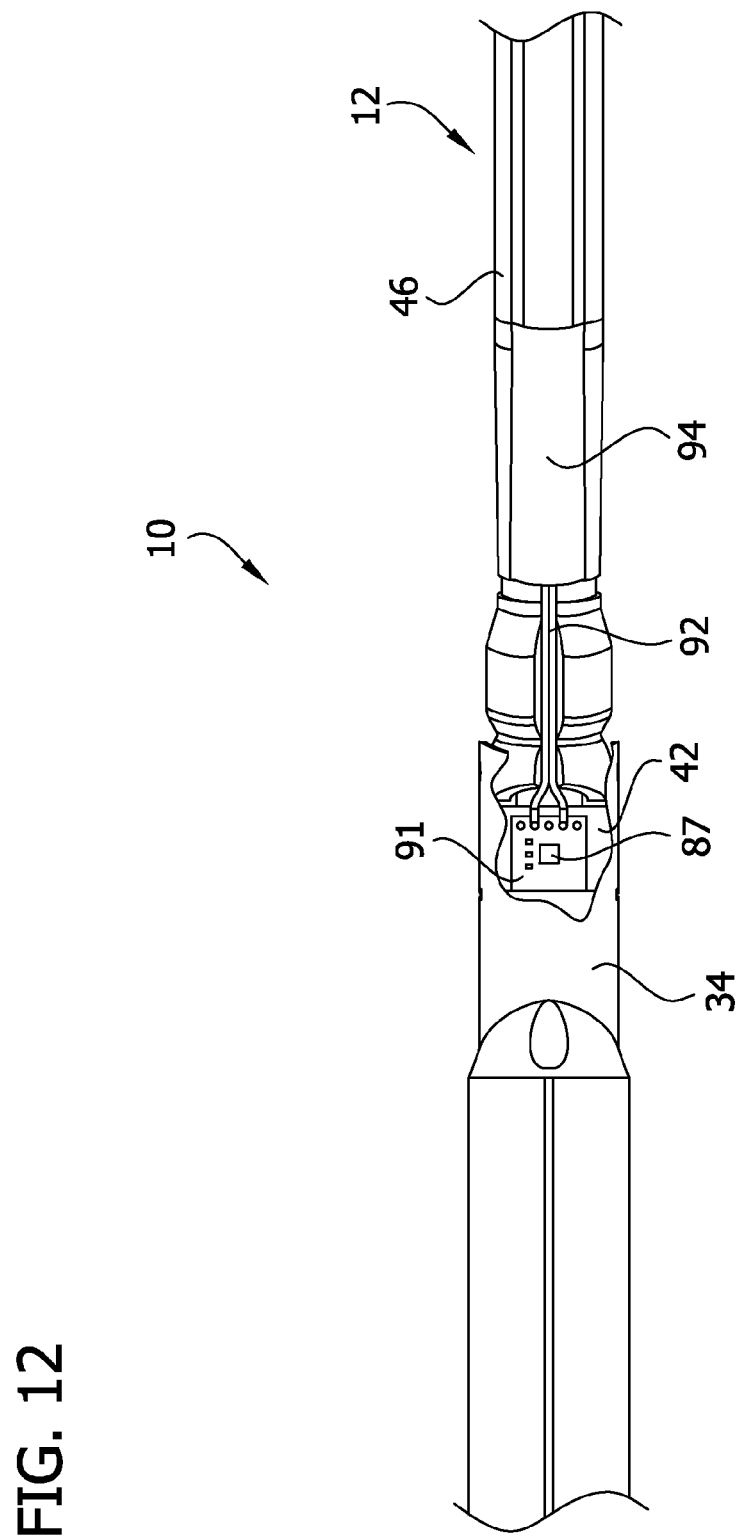
FIG. 12 is an enlarged fragmentary bottom elevation of the catheter body, including portions broken away to show underlying components.

As shown in FIG. 12 (and also shown in FIG. 2), the illustrated catheter 10 includes an angular-displacement sensor 87 in addition to the angular-positioning mechanism 60. In other embodiments the catheter 10 may include one of the angular-positioning mechanism 60 and the angular-displacement sensor 87, and not the other. The angular-displacement sensor 87 is used for determining the angular tissue-removing position of the tissue-removing element 16 relative to longitudinal axis A2 of the body lumen BL. In the illustrated embodiment, the angular-positioning mechanism 60 and the angular-displacement sensor 87 together allow the user to determine the angular tissue-removing position of the tissue-removing element in the body lumen BL during treatment and adjust this angular position a selected magnitude and/or direction, without manually rotating or torqueing the second (proximal) longitudinal end body portion 48 of the catheter body 12.

Referring still to FIG. 12 (also shown in FIG. 2), the angular-displacement sensor 87 is associated with the first (distal) longitudinal end body portion 46 of the catheter body 12 and is configured to detect the angular displacement of the apposition member 52 (and the angular tissue-removing position of the tissue-removing element 16 relative to the longitudinal axis A2 of the body lumen BL). In the illustrated embodiment, the angular-displacement sensor 16 is fixedly secured to the housing 34, and more particularly, to the cam follower or ramp 42 within the housing. A bottom side of the ramp 42 has a cutout or recess 88 (see FIG. 2) in which the angular-displacement sensor 87 is received. In the illustrated embodiment, the angular-displacement sensor 87 is a solid-state sensor, such as an integrated circuit mounted on a circuit board 90. For example, in one embodiment the angular-displacement sensor 87 may be a gyroscope. The angular-displacement sensor 87 may be other types of sensors, other than a gyroscope. For example, the angular-displacement sensor 87 may be a magnetometric sensor, which is used to determine the angular tissue-removing position of the tissue-removing element 16 relative to the magnetic fields of the earth. The angular-displacement sensor 87 may be secured to the catheter body 12 at other locations for detecting the angular displacement of the apposition member 52 and the displacement of the angular tissue-removing position of the tissue-removing element 16. The catheter 10 includes one or more electrical conductors 92 (e.g., wires) electrically connected to the angular-displacement sensor 87 and running along the catheter body 12 toward the proximal end 12a of the body. In particular, the electrical conductors 92 are received in a wire lumen 94 at the first (distal) longitudinal body portion 46 and in the wire lumen 78 at the second (proximal) longitudinal body portion 48. The lumens 78, 94 are separate and free from communication with the driveshaft lumens 70, 72. The electrical conductors 92 are electrically connectable to a control circuit 94 and the power source 21. The control circuit 94 may be provided in the handle 14, as illustrated, or the control circuit may be provided in the catheter body 12, such as on the same circuit board 91 as the angular-displacement sensor 87.

Figure 13:
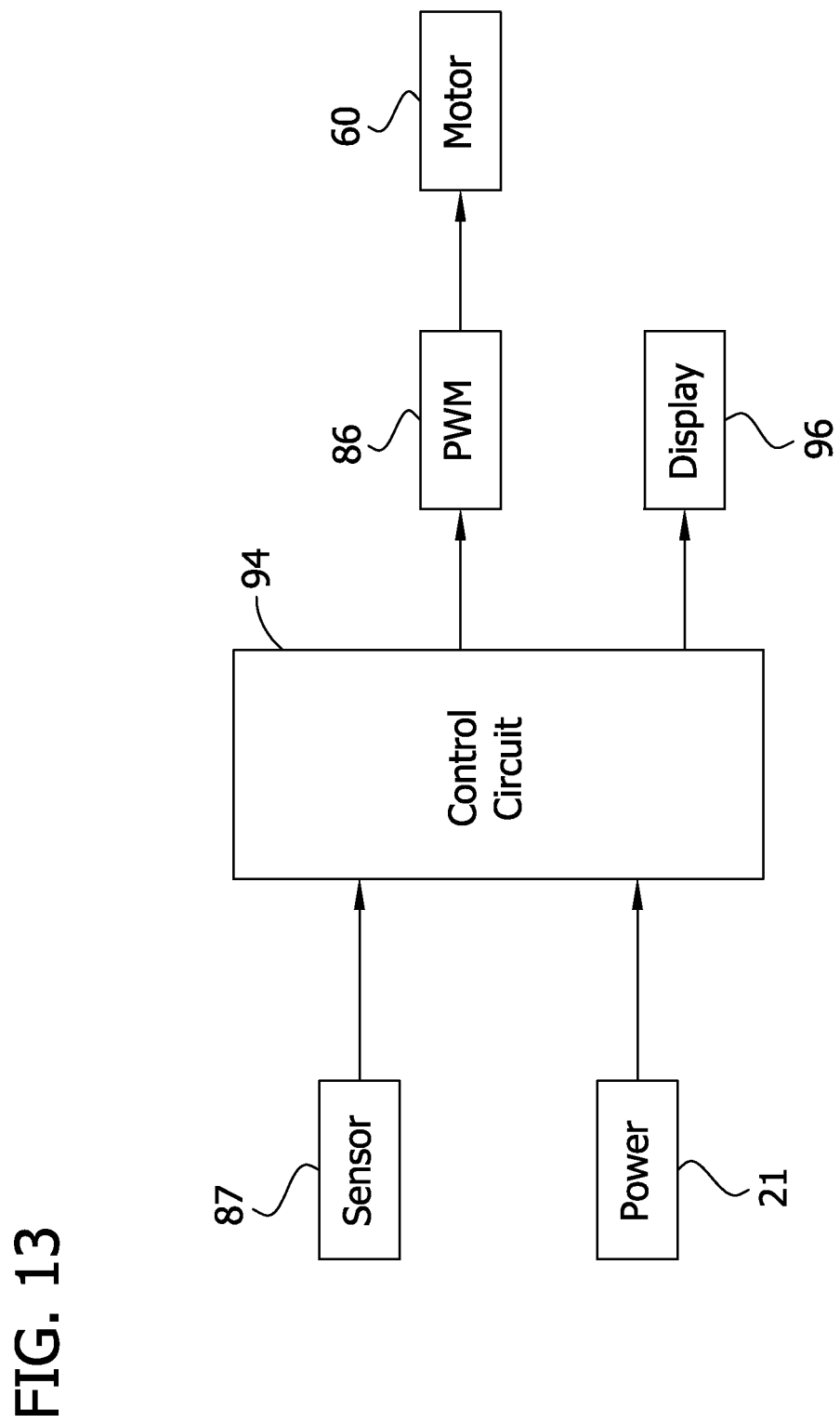
FIG. 13 is a block diagram illustrating a control circuit and components in communication with the control circuit according to the embodiment illustrated in FIG. 9.

Referring to FIG. 13, in the illustrated embodiment, the control circuit 94 is configured (e.g., programmed) to receive electrical signals from the angular-displacement sensor 87, compute the angular displacement of the tissue-removing element 16, and communicate the magnitude and direction of the displacement to the user via a user interface 96. In the illustrated embodiment, the user interface 96 comprises a display (e.g., an LCD screen or other electronic display screen) on the handle 14 (See FIGS. 1 and 10). As explained in more detail below when discussing an exemplary method of use, the control circuit 94 is configured (e.g., programmed) to compute the angular displacement of the tissue-removing element 16 (and/or the angular displacement of the apposition member 52) relative to a reference angular tissue-removing position based on the electrical signals received from the angular-displacement sensor 87. The control circuit 94 then displays the computed angular displacement on the display 96 for the user, such as illustrated in FIG. 10. Thus, as the user actuates operation of the angular-positioning motor 60, the user can observe the displayed angular displacement on the display 96 as feedback to make a determination as to the contemporaneous angular tissue-removing position of the tissue-removing element 16 in the body lumen BL. As also shown in FIG. 13, the power source 21 and the pulse width modulator(s) 86 may be in electrical communication with the control circuit 94. The control circuit monitors the amount of electrical power being drawn by angular-positioning motor 60 and/or the driveshaft motor 30. Based on the amount of electrical power being supplied to one or both of the motors 60, 30, the control circuit 94 can adjust the duty cycle supplied to the angular-positioning motor 60, through communication with the pulse width modulator(s) 86, to ensure that the motor rotates at a desired speed.

Figure 11:
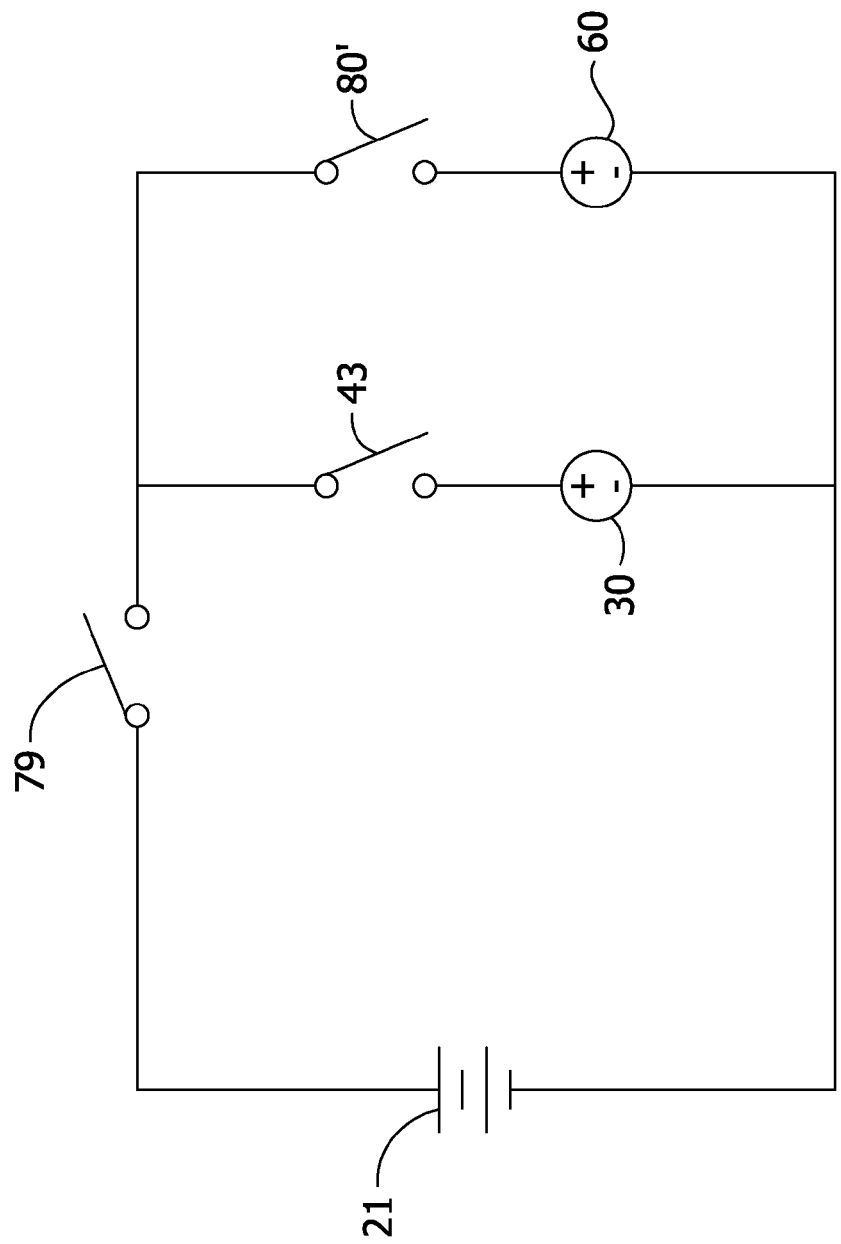
FIG. 11 is an electrical diagram of electrical components of the catheter according to one or more embodiments.
Figure 14:
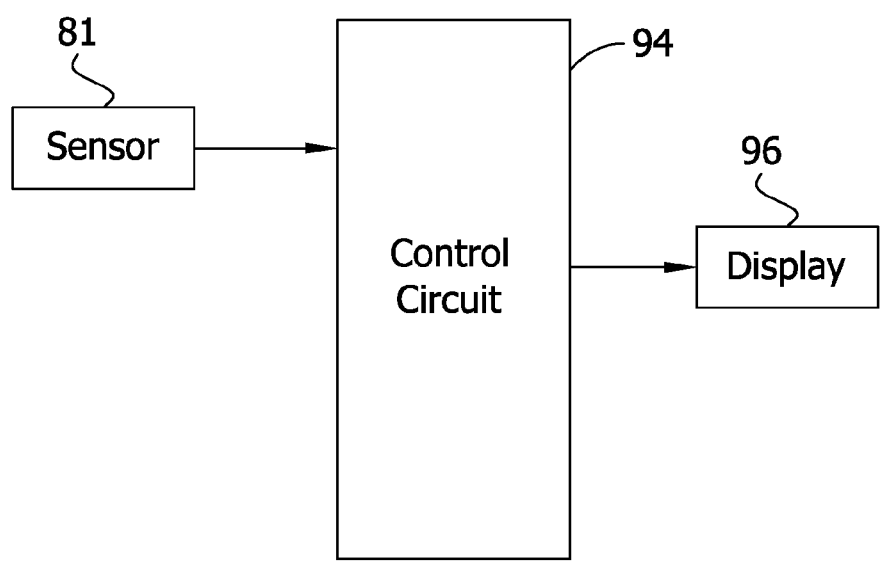
FIG. 14 is a block diagram illustrating a control circuit and components in communication with the control circuit according to the embodiment illustrated in FIG. 11.

FIG. 14 illustrates an electrical diagram for the embodiment illustrated in FIG. 11. As shown in FIG. 14, the control circuit 94 is in electrical communication with the sensor 87 and the display 96 in the manner set forth above with respect to FIG. 13. However, in this example the catheter 10 does not include a pulse width modulator, so the control circuit is not in communication with the power source 21 or the angular-positioning motor 60 for regulating power supplied to the motor.

In an exemplary method of using the illustrated catheter 10, the distal end 12b of the catheter body 12 may be inserted into the body lumen BL defined by the blood vessel V, such as a peripheral artery of a patient's leg, and traversed through the body lumen to a target site. For example, the target site may be a stenotic lesion T (i.e., build-up of plaque) in the vessel V. Upon reaching the target site T in the vessel V and prior to deploying the tissue-removing element 16, the control circuit 94 may compute the contemporaneous angular tissue-removing position of the tissue-removing element 16 and store the computed angular position in the memory as a reference angular tissue-removing position. In the illustrated example, the power actuator 81 may activate the angular position sensor 87, and the control circuit 94 is programmed to store the first computed contemporaneous angular tissue-removing position of the tissue-removing element 16 as the reference angular tissue-removing position. In another example, the user interface (e.g., display) 96 may be configured to allow the user to instruct the control circuit 94 when to store a computed contemporaneous angular tissue-removing position of the tissue-removing element 16 as the initial or reference angular tissue-removing position. For example, the display 96 may be a touch-screen that includes a graphical image (not shown) for allowing the user to select when to store a computed contemporaneous angular tissue-removing position of the tissue-removing element 16 as the reference angular tissue-removing position. In yet another example, upon the first deployment of the tissue-removing element 16 and activation of the driveshaft motor 30 (such as by sliding the actuator 40 proximally), the control circuit 94 may compute and store the contemporaneous angular tissue-removing position of the tissue-removing element 16 as the initial angular tissue-removing position. Other ways of setting and storing the initial angular tissue-removing position of the tissue-removing element 16 do not depart from the scope of the present invention.

After computing the reference angular position of the tissue-removing element 16, the control circuit 94 may be programmed to communicate to the user that the tissue-removing element 16 is positioned at 0 degrees. For example, the display 96 (e.g., an LCD display or other display) may read "0°." With the tissue-removing element 16 in the initial or reference angular tissue-removing position, the user may deploy the tissue-removing element 16 (such as in the manner set forth above) and with driveshaft motor 30 rotating the tissue-removing element, the user may make an initial "tissue-removing pass" through the stenotic lesion T by moving the catheter body 12 distally through the body lumen BL, such that the tissue-removing element cuts the stenotic lesion at the initial angular location within the body lumen BL.

During the tissue-removing pass, there may be a tendency for the catheter body 12 to rotate or become angularly displaced during a tissue-removing pass because the distal end 12b tends to travel along a path of least resistance in the body lumen BL. This tendency of the distal end 12b of the catheter body 12 to travel along a path of least resistance may be referred to as "guttering," when the tissue-removing element 16 deviates from its angular tissue-removing position. In one example, the control circuit 94 may be configured (e.g., programmed) to continue to receive signals from the angular-displacement sensor 87 and compute and display the angular displacement of the tissue-removing element within the body lumen BL. Accordingly, as the user is moving the catheter body 12 distally, the user can observe the angular tissue-removing position, which corresponds to the angular position of the "tissue-removing pass" within the body lumen BL. In one example, the control circuit 94 may be programmed (i.e., configured) to inhibit power from being supplied to the angular-positioning motor 60 when the tissue-removing element 16 is deployed, thereby inhibiting the user from adjusting the angular tissue-removing position of the tissue-removing element during a tissue-removing pass. Thus, if the user is notified that the tissue-removing element 16 has deviated from the desired angular location, the user can store the tissue-removing element 16, move the catheter body 12 proximally, and then attempt to make another tissue-removing pass in an attempt to avoid guttering. Alternatively, where the control circuit 94 is not programmed to inhibit power from being supplied to the angular-positioning motor 60 when the tissue-removing element 16 is deployed, the user may make adjustments to the angular tissue-removing position, such as by using the actuator 82, to maintain the tissue-removing element 16 at the desired angular tissue-removing position during a tissue-removing pass. In another example, the control circuit 94 may be configured (e.g., programmed) to indicate to the user that the tissue-removing element 16 has deviated from the desired angular location within the body lumen (i.e., deviated a selected threshold magnitude, such as 20 degrees or 15 degrees or 10 degrees or 5 degrees). For example, the control circuit 94 may be configured (i.e., programmed) to flash the read-out on the display 96 or activate another audio or visual indicator, such as an LED on the handle.

After making the initial tissue-removing pass, the tissue-removing element 16 may be moved to its non-deployed position (such as in a manner described above), and the catheter body 12 may be moved proximally, toward the proximal end of the target site within the body lumen BL. The user may check the lesion T under fluorescence or other imaging means to make a determination of the desired angular location of the next tissue-removing pass through the lesion. The user may then adjust the angular tissue-removing position of the tissue-removing element 16 by using the actuator 82, and then deploy the tissue-removing element and move the catheter body 12 distally to make the desired second tissue-removing pass. After making the second tissue-removing pass, the above steps of i) storing the tissue-removing element 16, ii) moving the catheter proximally to a proximal location of the body lesion T, iii) checking the lesion under fluorescence to make a determination of the next desired tissue-removing pass through the lesion, iv) adjusting the angular tissue-removing position of the tissue-removing element to a desired position, and v) making an additional "tissue-removing pass" through the lesion, are repeated a desired number of times. The desired angular tissue-removing position of the tissue-removing element 16 may be made relative to the initial reference angular position of the first tissue-removing pass. Alternatively, the control circuit 94 may be configured to allow the user to selectively change the stored reference angular position used for subsequent tissue-removing passes. For example, after making the second tissue-removing pass, the user may choose to change the reference angular tissue-removing position for the third tissue-removing pass to be the angular location of the second tissue-removing pass, as opposed to the angular location of the first tissue-removing pass.

As an example, as shown schematically in FIG. 7, the user may desire to make a second tissue-removing pass at a peripheral portion of the body lumen BL that is offset about 30 degrees clockwise from the initial tissue-removing pass. Accordingly, the user may depress the right side of the toggle actuator 82 to activate the prime mover 60 and clockwise rotation of the apposition member 52, thus adjusting the angular tissue-removing position of the tissue-removing element 16. As the user holds down the right side of the toggle actuator 82 (alternatively, the right side of the toggle may remain depressed) and the apposition member 52 and first (distal) longitudinal body portion 46 rotates clockwise, the user observes the readout on the display 96, which indicates the magnitude and direction of the angular displacement of the tissue-removing position of the tissue-removing element 16. For example, a "+" indicates that the angular displacement of the angular tissue-removing position of the tissue-removing element 16 is in the clockwise direction, and a "−" indicates that the angular tissue-removing displacement is in the counterclockwise direction. When the display 96 reads "+30°" or some other readout corresponding to the desired angular displacement, the user disengages the right side of the toggle actuator 82 (alternatively, the user moves the toggle actuator to its center "off"

position), so that the angular-positioning motor 60 deactivates and ceases rotation of the apposition member 52. Next, the tissue-removing element 16 is deployed, such that the tissue-removing element 16 engages a peripheral portion of the body lumen BL that is about 30 degrees offset, in the clockwise direction, from the peripheral portion of the body lumen of the first tissue-removing pass, and the user makes the second tissue-removing pass. Subsequent tissue-removing passes may be made in the same fashion.

Figure 15:
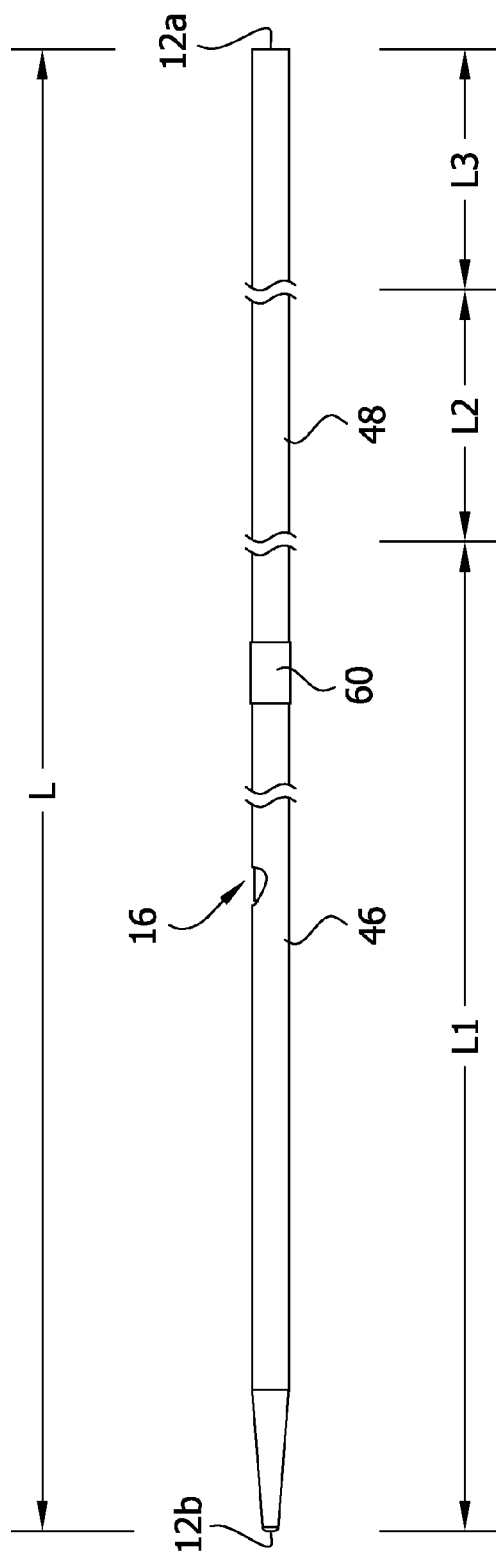
FIG. 15 is a schematic of the catheter body shown in a linear configuration.

As disclosed above, in other embodiments the catheter 12 includes the angular-positioning mechanism 60, but does not include an angular-displacement sensor 87. Instead, the user may determine the angular tissue-removing position of the tissue-removing element 16 solely through fluorescence or other imaging means. This catheter 12 has the benefit of allowing the user to automatically (i.e., non-manually) adjust the angular tissue-removing position of the tissue-removing element 16. Moreover, as shown in FIG. 15, because the angular-positioning mechanism 60 (e.g., the angular-positioning motor) is within the first three-quarter length L3 of the catheter body 12 (e.g., adjacent the apposition member), the torsional load applied by the angular-positioning mechanism is not applied along the full length L of the catheter body 12, thereby making it more likely that the torsional force will be imparted substantially entirely along the length of the first (distal) longitudinal body portion 46 (i.e., rotation of the first (distal) longitudinal body portion, and thus the apposition member, is substantially commensurate with rotation of the prime mover), rather than a portion or all of the torsional load being stored within the first (distal) longitudinal body portion (known as "lag") and possibly released at a later time (known as "whip"). For example, where the angular-positioning motor 60 and the first (distal) longitudinal body portion 46 have a 1:1 ratio (i.e., 1 revolution of the motor equals 1 revolution of the first (distal) longitudinal body portion and the apposition member) torsional load, it may be more likely that rotational of motor degrees imparts 30 degrees of rotation to both the first (distal) longitudinal body portion and the apposition member 52 about the rotational axis A2 than if the torsional load was applied at the proximal end 12*a* of the catheter body 12.

As also disclosed above, in other embodiments the catheter 10 includes the angular-displacement sensor 87, but does not include the angular-positioning mechanism 60. In such an embodiment, the angular tissue-removing position of the tissue-removing element 87 may be adjusted in the body lumen BL in a conventional manner, such as by rotating or torqueing the proximal end 12*a* of the catheter body 12 outside the body of the patient. The user receives feedback as to the angular tissue-removing position of the tissue-removing element 16 through the display 96 or in other communication means, such as other audio, visual, or tactile ways. The catheter 10 including the angular-displacement sensor 87 has the benefit of facilitating more accurate and precise tissue removal because the user has the ability to receive real-time feedback regarding the angular tissue-removing position of the tissue-removing element 16 as the catheter is removing tissue from the body lumen BL. For example, as described above, the user may be able to determine if the distal end 12*b* of the catheter body 12 is "guttering" and then make necessary adjustments to the catheter 10, as described above.

In another embodiment, the control circuit 94 (or another control circuit) of the catheter 10 may be electrically connected to (i.e., in communication with) both the angular-positioning motor 60, for controlling operation of the motor, and the angular-displacement sensor 87, for receiving feedback as to the angular tissue-removing position of the tissue-removing element 16. Accordingly, as opposed to the first embodiment where the user directly controls the operation of the angular-positioning motor 60, in this embodiment the user inputs the desired (i.e., inputted) angular tissue-removing position of the tissue-removing element 16 to the control circuit 94, and the control circuit controls the angular-positioning motor to move the tissue-removing element 16 to the desired angular tissue-removing position. Unless otherwise indicated, the present embodiment of the catheter is identical to the first embodiment, with like components being indicated by corresponding reference numerals, and the same teachings set forth with respect to the first embodiment apply equally to the present embodiment.

Figure 16:
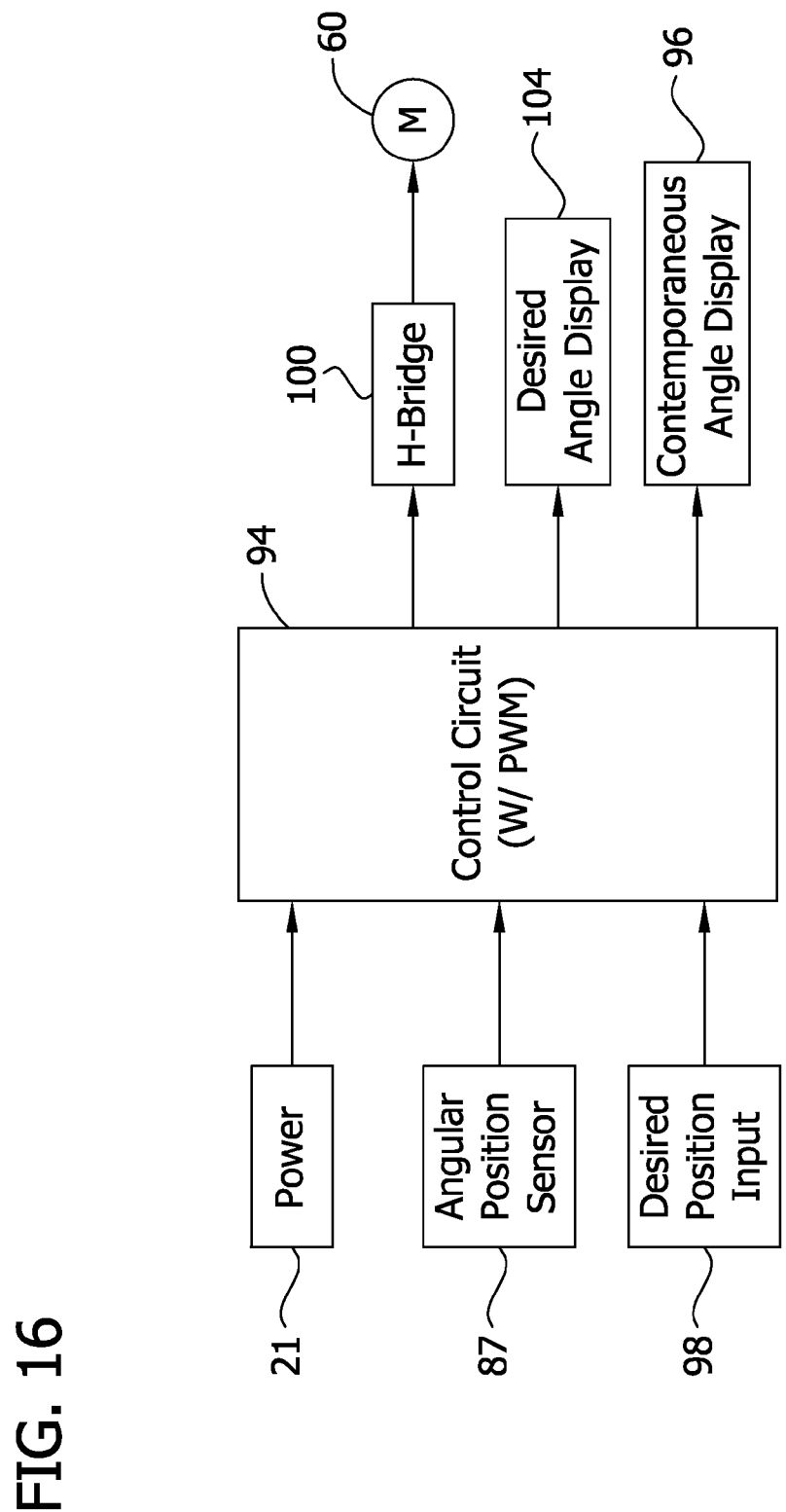
FIG. 16 is a block diagram illustrating a control circuit and components in communication with the control circuit according to one or more embodiments.

FIG. 16 illustrates an exemplary block diagram of the present embodiment, showing electrical components of the catheter 10 in communication with the control circuit 94. In this example, the control circuit 94 receives respective input signals from the following components: the power source 21 for regulating electrical power to the angular-positioning motor 60; the angular-displacement sensor 87 to determine the contemporaneous angular tissue-removing position of the tissue-removing element 16; and a user input 98 for allowing a user to input the desired angular tissue-removing position of the tissue-removing element to the control circuit 94. The power source 21 may be the same power source electrically connected to the driveshaft motor 30 (e.g., a battery in the handle), or a different power source. The angular position sensor 87 may be the same as described above, such as a gyroscope, and as illustrated in FIGS. 2 and 12. The control circuit 94 sends respective output signals to the following components: the contemporaneous angle display 96 for displaying the contemporaneous angular tissue-removing position of the tissue-removing element 16; the desired angle display 104 for displaying the desired tissue-removing position of the tissue-removing element; and an H-bridge 100 for enabling a voltage to be applied across the angular-positioning motor 60 in either direction to selectively drive the motor in the clockwise direction and the counterclockwise direction.

Figure 17:
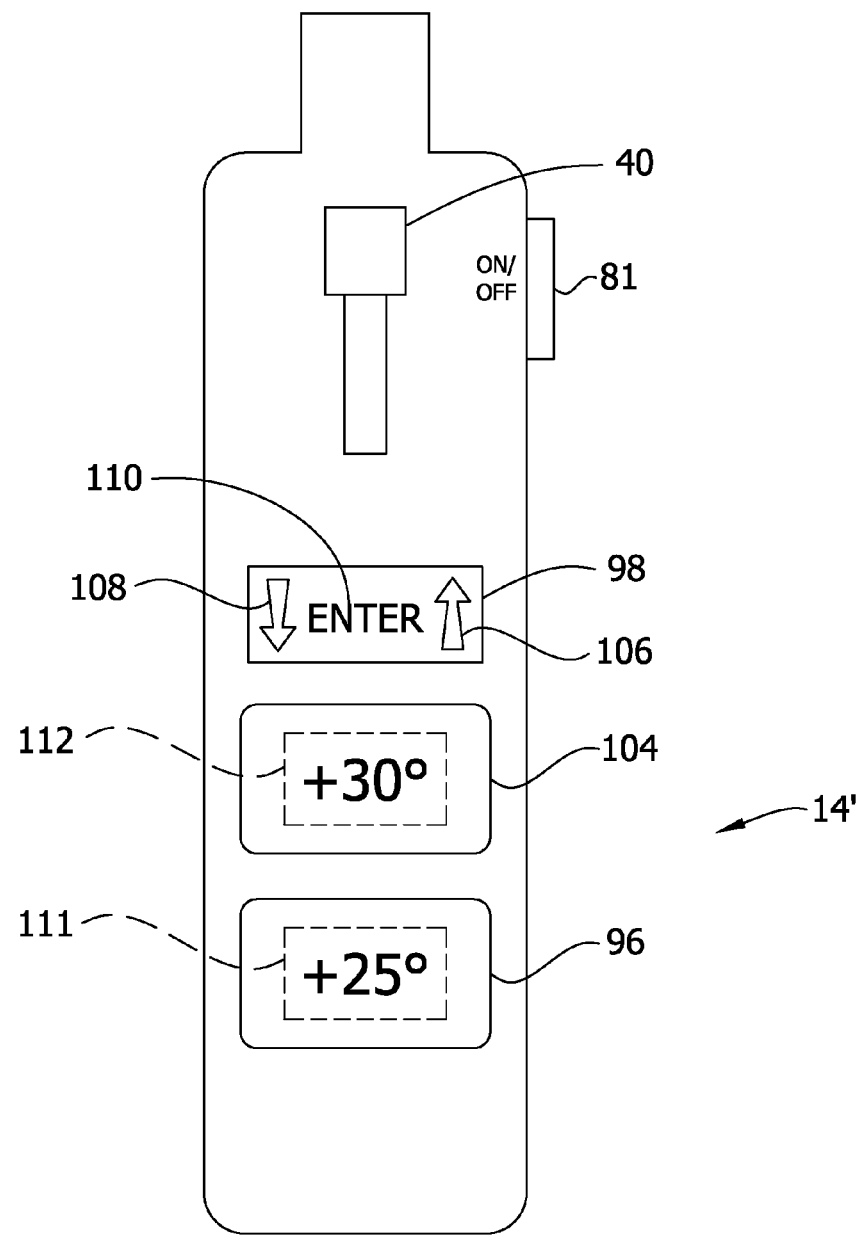
FIG. 17 is an enlarged schematic of one embodiment of a handle for use with the embodiment illustrated in FIG. 16.

Referring to FIG. 17, one embodiment of a handle (or control unit), including some of the electrical components shown in FIG. 16, is generally indicated at 14'. Unless otherwise indicated, the present embodiment of the handle 14' is identical to the first handle 14, with like components being indicated by corresponding reference numerals, and the same teachings set forth with respect to the first embodiment apply equally to the present embodiment. Although not illustrated, the control circuit 94, the power source 21, the driveshaft motor 30, and the H-bridge 100 may be provided in the handle 14'. In the illustrated embodiment, the user input 98 is in the form of a touchscreen display (e.g., an LCD touchscreen) on the handle 14'. The control circuit 94 is configured to generate graphical icons on the user input display 98, such as an up arrow (↑) 106, a down arrow (↓) 108, and the word "ENTER" 110, as illustrated, to allow the user to communicate to the control circuit the desired amount of rotation of the tissue-removing element 16 in the body lumen BL. The control circuit 94 is configured to generate graphical image(s) 111 on the contemporaneous angle display 96, to communicate the contemporaneous angular tissue-removing position of the tissue-removing element 16 to the user, and graphical image(s) 112 on the desired angle display 104, to communicate the selected desired angular tissue-removing position to the user.

The control circuit 94 and the user input 98 are configured so that the user touches a respective one of the up and down arrows 106, 108, respectively, generated on the display to communicate to the control circuit the magnitude and direction that the user desires to change the angular tissue-removing position of the tissue-removing element 16. In the illustrated embodiment, the up arrow 106 indicates a change in angular position in the clockwise direction, and the down arrow 108 indicates a change in angular position in the counterclockwise direction. In one embodiment, the number of discrete times the selected arrow 106, 108 is touched and/or the amount of time the selected arrow is continuously touched, communicates a selected the magnitude to the control circuit 94 to change the angular tissue-removing position of the tissue-removing element 16 in the selected direction. This magnitude is stored in the memory and the control circuit 94 changes the graphical image 112 on the desired angular position display 104 to reflect the adjustment. In the illustrated embodiment, a positive graphical symbol ("+") indicates angular displacement of the tissue-removing element 16 in the clockwise direction relative to a reference angular position, and a negative graphical symbol ("−") indicates angular displacement in the counterclockwise direction relative to a reference angular position.

When the desired angle is presented on the display 96 (as represented by the graphical number "+30" in FIG. 17), the user may touch the "ENTER" icon to thereby instruct the control circuit 94 to move the tissue-removing element 16 to angular tissue-removing position presented on the display 104, which is also stored in memory. The control circuit 94 communicates with the angular-positioning motor 60 to adjust the tissue-removing element 16. The display 96, which may be similar or identical to the corresponding display of the prior handle embodiment, outputs the contemporaneous angular tissue-removing position of the tissue-removing element 16, as computed by the control circuit 94 using signals from the angular position sensor 87. The control circuit 94 may use the signals from the angular position sensor 87 as feedback for positioning the tissue-removing element. In another example, the control circuit 94 may be configured to adjust the angular tissue-removing position of the tissue-removing element 16 in other ways. For example, the control circuit 94 may be configured (e.g., programmed) to supply the angular-positioning motor 60 with a pre-selected amount of power for a pre-selected amount of time to adjust the tissue-removing element 16 to the desired (i.e., inputted) angular tissue-removing position.

Because the control circuit 94 controls the angular tissue-removing position of the tissue-removing element 16, in one or more embodiments the control circuit may be configured to maintain the tissue-removing element 16 in substantially the desired (i.e., inputted) angular tissue-removing position, as the user is making a tissue-removing pass in the body lumen BL. In this embodiment, the control circuit 94 uses the signals from the angular position sensor 87 as feedback for maintaining the tissue-removing element in its selected angular tissue-removing position in the body lumen BL. This embodiment is meant to counteract the tendency of distal end 12b of the catheter body 12 to gutter during a tissue-removing pass and inhibit the tissue-removing element 16 from deviating from the desired and selected angular position of the tissue-removing pass.

In one embodiment, the catheter 10 may be configured to restrict or limit the amount of rotation of the apposition member 52 and the first (distal) longitudinal body portion 46 about the rotation axis A2. For example, the control circuit 94 may be programmed to inhibit the user from rotating beyond about 360 degrees. That is, the control circuit 94 may be programmed to use the signals from the angular position sensor 87 as feedback and inhibit the user from increasing the angular position of the tissue-removing element beyond about 360 degrees from the initial reference position. The catheter 10 may also include an indicator, such as a visual indicator (e.g., and LED), audio indicator, or tactile indicator, on the handle 14' to communicate to the user that the tissue-removing element 16 has reached a maximum allowable angular displacement and further rotation of the tissue-removing element 16 in the same direction is inhibited. Without restricting the amount of rotation of the first (distal) longitudinal body portion 46, a guidewire (not shown) may wrap around and become tangled with the catheter body 12. Moreover, the rotating the apposition member 52 and the first (distal) longitudinal body portion 46 more than 360 degrees may place undue tension on the electrical conductors 92 (e.g., wires) connecting the sensor 87 to the handle 14, which may damage the connections between the conductors and the sensor and the handle. Other ways of restricting rotation of the apposition member 52 and the first (distal) longitudinal body portion 46 about the rotation axis A2 do not depart from the scope of the present invention. In one example, the catheter 10 may include a mechanical stop, such as a stop adjacent the prime mover 60, for inhibiting the prime mover from rotating more than about 360 degrees.

Although the control circuit 94 is illustrated as a single, integrated circuit throughout the drawings and the above-described embodiments, it is understood that the control circuit may include separate, individual control circuits (e.g., separate microcontrollers), each dedicated to one of the prime mover and the angular-displacement sensor.

Having described the invention in detail, it will be apparent that modifications and variations are possible without departing from the scope of the invention defined in the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue from a body lumen having a longitudinal axis, the tissue-removing catheter comprising:
   a catheter body configured for insertion in the body lumen, the catheter having a proximal end, a distal end, a longitudinal axis extending between the proximal and distal ends, wherein the catheter body includes a first longitudinal body portion adjacent the distal end, and a second longitudinal body portion proximal of the first longitudinal body portion, the first longitudinal body portion defining a side opening;
   a tissue-removing element disposed in the first longitudinal body portion of the catheter body, wherein the tissue-removing element is extendable outside the first longitudinal body portion through the side opening; and
   a tissue-removing driveshaft extending longitudinally within the first and second longitudinal body portions of the catheter body and configured for rotation about its longitudinal axis relative to the catheter body, the tissue-removing driveshaft operatively connected to the tissue-removing element to impart rotation to the tissue-removing element relative to the catheter body, wherein the first longitudinal body portion is rotatable about an axis extending along its length and relative to the second longitudinal body portion to adjust the angular position of the first longitudinal body portion and the side opening relative to the second longitudinal body portion, an angular-positioning mechanism disposed between the first and second longitudinal body portions and operatively connected to the first longitudinal body portion and configured to rotate the first longitudinal body portion about the axis extending along its length and relative to the second longitudinal body portion to adjust the angular position of the first longitudinal body portion and the side opening relative to the second longitudinal body portion.

2. The tissue-removing catheter set forth in claim 1, wherein the angular-positioning mechanism comprises a prime mover.

3. The tissue-removing catheter set forth in claim 2, wherein the prime mover comprises a through hole motor defining a through opening, and wherein the tissue-removing driveshaft passes through the through opening of the through hole motor.

4. The tissue-removing catheter set forth in claim 2, further comprising:
a control unit attachable to the catheter generally adjacent the proximal end of the catheter body, the control unit being operatively connectable to the prime mover for controlling operation of the prime mover.

5. The tissue-removing catheter set forth in claim 4, wherein the control unit includes a control circuit for sending electrical control signals to the prime mover to control operation of the prime mover, and a user interface allowing a user to communicate with the control circuit.

6. The tissue-removing catheter set forth in claim 1, wherein the first longitudinal body portion includes an apposition member configured to impart an apposition force in a generally radial direction relative to the longitudinal axis of the catheter body to position the tissue-removing element in an angular tissue-removing position when the catheter body is inserted in the body lumen, wherein the apposition member is rotatable with the first longitudinal body portion.

7. The tissue-removing catheter set forth in claim 1, further comprising:
an angular-displacement sensor coupled to the first longitudinal body portion and configured to detect an angular displacement of the first longitudinal body portion relative to the second longitudinal body portion.

8. The tissue-removing catheter set forth in claim 1, wherein the tissue-removing element is coupled to the first longitudinal body portion such that rotation of the first longitudinal body portion about the axis extending along its length and relative to the second longitudinal body portion adjusts an angular tissue-removing position of the tissue-removing element.

9. A tissue-removing catheter for removing tissue from a body lumen having a longitudinal axis, the tissue-removing catheter comprising:
a catheter body configured for insertion in the body lumen, the catheter having a proximal end, a distal end, and a longitudinal axis extending between the proximal and distal ends, wherein the catheter body includes a first longitudinal body portion adjacent the distal end, and a second longitudinal body portion proximal of the first longitudinal body portion; a tissue-removing element coupled to the catheter body and configured to be positioned in an angular tissue-removing position relative to the longitudinal axis of the body lumen when the catheter body is inserted in the body lumen, the tissue-removing element being rotatable relative to the second longitudinal body portion about a rotational axis to adjust the angular tissue-removing position of the tissue- removing element relative to the longitudinal axis of the body lumen when the catheter body is inserted in the body lumen;

a tissue-removing driveshaft extending longitudinally within the catheter body and configured for rotation about its longitudinal axis relative to the catheter body, the tissue-removing driveshaft operatively connected to the tissue-removing element to impart rotation to the tissue-removing element relative to the catheter body; and a through hole motor disposed between the first and second longitudinal body portions and operatively connected to the tissue-removing element and configured to rotate the tissue-removing element relative to the second longitudinal body portion about the rotational axis to adjust the angular tissue-removing position of the tissue-removing element, relative to the longitudinal axis of the body lumen, from a first angular tissue-removing position to a second angular tissue-removing position offset from the first angular tissue-removing position, the through hole motor defining a through opening, wherein the tissue-removing driveshaft passes through the through opening of the through hole motor.

10. The tissue-removing catheter set forth in claim 9, wherein the through hole motor is operatively connected to the first longitudinal body portion for rotating the tissue-removing element relative to the second longitudinal body portion about the rotational axis to adjust the angular tissue-removing position of the tissue-removing element, relative to the longitudinal axis of the body lumen.

11. The tissue-removing catheter set forth in claim 9, further comprising an apposition member configured to impart an apposition force in a generally radial direction relative to the longitudinal axis of the catheter body to position the tissue-removing element in the angular tissue-removing position when the catheter body is inserted in the body lumen, wherein the through hole motor is operatively connected to the apposition member to impart selective rotation to the apposition member, relative to the second longitudinal body portion of the catheter body.

12. The tissue-removing catheter set forth in claim 9, further comprising: a control unit attachable to the catheter generally adjacent the proximal end of the catheter body, the control unit being operatively connectable to the through hole motor for controlling operation of the through hole motor.

13. The tissue-removing catheter set forth in claim 12, wherein the control unit includes a control circuit for sending electrical control signals to the through hole motor to control operation of the through hole motor, and a user interface allowing a user to communicate with the control circuit.

14. The tissue-removing catheter set forth in claim 9, further comprising:

an angular-displacement sensor generally adjacent the tissue-removing element, the angular-displacement sensor configured to detect an angular displacement of the angular tissue-removing position of the tissue-removing element imparted by the through hole motor.

15. The tissue-removing catheter set forth in claim 14, wherein the angular-displacement sensor is operatively connected to the tissue-removing element such that the angular-displacement sensor rotates in conjunction with rotation of the tissue-removing element imparted by the through hole motor.

16. The tissue-removing catheter set forth in claim 14, further comprising a control unit attachable to the catheter body generally adjacent the proximal end of the catheter body, the control unit being operatively connectable to:
  the through hole motor for controlling operation of the through hole motor; and
  the angular-displacement sensor for receiving signals from the angular-displacement sensor indicative of the angular displacement of the angular tissue-removing position of the tissue-removing element imparted by the through hole motor.

17. The tissue-removing catheter set forth in claim 9, further comprising:
  a second longitudinal lumen defined by the catheter body and extending lengthwise of the catheter body, the second longitudinal lumen being separate from the first longitudinal lumen; and
  at least one first electrical wire electrically coupled to the through hole motor and extending within the second longitudinal lumen toward the proximal end of the catheter body.

\* \* \* \* \*